(12) United States Patent
Samoto et al.

(10) Patent No.: US 9,107,428 B2
(45) Date of Patent: Aug. 18, 2015

(54) FRACTIONATED SOYBEAN PROTEIN MATERIAL, PROCESSED SOYBEAN SUITABLE FOR THE MATERIAL, AND PROCESSES FOR PRODUCTION OF THE SOYBEAN PROTEIN MATERIAL AND THE PROCESSED SOYBEAN

(75) Inventors: Masahiko Samoto, Tsukubamirai (JP); Motohiro Maebuchi, Tsukubamirai (JP); Chiaki Miyazaki, Tsukubamirai (JP); Hirofumi Kugitani, Tsukubamirai (JP); Mitsutaka Kohno, Izumisano (JP); Kensuke Fukui, Izumisano (JP); Motohiko Hirotsuka, Tsukubamirai (JP)

(73) Assignee: FUJI OIL COMPANY, LIMITED, Osaka (JP)

( * ) Notice: Subject to any disclaimer, the term of this patent is extended or adjusted under 35 U.S.C. 154(b) by 2239 days.

(21) Appl. No.: 11/921,237

(22) PCT Filed: May 30, 2006

(86) PCT No.: PCT/JP2006/310751
§ 371 (c)(1),
(2), (4) Date: Nov. 29, 2007

(87) PCT Pub. No.: WO2006/129647
PCT Pub. Date: Dec. 7, 2006

(65) Prior Publication Data
US 2009/0232958 A1    Sep. 17, 2009

(30) Foreign Application Priority Data

May 30, 2005  (JP) .................................. 2005-157871
Mar. 3, 2006  (JP) .................................. 2006-057941

(51) Int. Cl.
*A23J 1/14*     (2006.01)
*A23C 11/10*    (2006.01)
(Continued)

(52) U.S. Cl.
CPC ................. *A23C 11/103* (2013.01); *A23J 1/14* (2013.01); *A23J 3/16* (2013.01); *A23L 1/2005* (2013.01); *A23V 2002/00* (2013.01)

(58) Field of Classification Search
USPC ........................................................ 426/634
See application file for complete search history.

(56) References Cited

U.S. PATENT DOCUMENTS 6,171,640 B1    1/2001    Bringe

FOREIGN PATENT DOCUMENTS

EP    1 174 516    1/2002
EP    1 323 353    7/2003
(Continued)

OTHER PUBLICATIONS

Hosoki, JP 10004907 A, Derwent Abstract.*
(Continued)

*Primary Examiner* — Elizabeth Gwartney
(74) *Attorney, Agent, or Firm* — Wenderoth, Lind & Ponack, L.L.P.

(57) ABSTRACT

Disclosed is a process for fractionating soybean protein into 7S globulin, 11S globulin or a lipophilic protein at a high purity with good efficiency, which relates to a fractionation technique for soybean protein into proteins having characteristic properties (7S globulin, 11S globulin and a lipophilic protein) and which is a process practicable at a food industrial level. It is found that soybean protein can be fractionated into 7S globulin, 11S globulin or a lipophilic protein at a high purity with good efficiency by extracting soybean milk from processed soybean which has been subjected to a water-in-solubilization treatment specific to a desired protein and fractionating the resulting soybean milk or soybean curd refuse into the desired protein.

8 Claims, 3 Drawing Sheets

(51) Int. Cl.
*A23J 3/16* (2006.01)
*A23L 1/20* (2006.01)

(56) References Cited

FOREIGN PATENT DOCUMENTS

| JP | 48-56843 | 11/1971 |
|---|---|---|
| JP | 49-31843 | 7/1972 |
| JP | 55-124457 | 9/1980 |
| JP | 58-36345 | 8/1982 |
| JP | 61-187755 | 8/1986 |
| JP | 5-43597 | 2/1993 |
| JP | 9-23838 | 1/1997 |
| JP | 2000-191694 | 7/2000 |
| WO | 00/58492 | 10/2000 |
| WO | 02/28198 | 4/2002 |
| WO | 2004/043160 | 5/2004 |

OTHER PUBLICATIONS

Fukuda et al. JP 2002 142685—Derwent Abstract.*
Fukada et al. JP 2002 142685—Machine Translation (Mar. 8, 2011).*
Albrecht et al. "Rate Studies on Atmospheric Steaming and Immersion Cooking of Soybeans" in Cereal Chemistry vol. 43, p. 400-407, 1966.*
Office Action dated Aug. 20, 2010 issued in corresponding Chinese Patent Application No. 200680019008.6 with its English translation.
Supplementary European Search Report issued Dec. 14, 2010 in European Patent Application No. 06746979.
M. Samoto et al., "Simple and Efficient Procedure for Removing the 34 kDa Allergenic Soybean Protein, *Gly m* I, from Defatted Soy Milk", Biosci. Biotech. Biochem., vol. 58, No. 11, pp. 2123-2125, 1994.
T. Okita et al., "Effects of Dietary Soybean Globulins on Plasma and Liver Lipids and on Fecal Excretion of Neutral Sterols in Rats", J. Nutr. Sci., Vitaminol., vol. 27, No. 4, pp. 379-388, 1981.
V. H. Thanh et al., "Major Proteins of Soybean Seeds. A Straightforward Fractionation and Their Characterization", J. Agric. Food Chem., vol. 24, No. 6, pp. 1117-1121, 1976.
E. M. Herman, Immunogold-Localization and Synthesis of an Oil-Body Membrane Protein in Developing Soybean Seeds, Planta, vol. 172, pp. 336-345, 1987.
M. Samoto et al., "Improvement of the Off-Flavor of Soy Protein Isolate by Removing Oil-Body Associated Proteins and Polar Lipids", Biosci. Biotechnol. Biochem., vol. 62, No. 5, pp. 935-940, 1998.
T. Nagano et al., "Relationship Between Rheological Properties and Conformational States of 7S Globulin from Soybeans at Acidic pH", Food Hydrocolloids: Structures, Properties and Functions, Plenum Press, New York, 1994, pp. 355-360.

* cited by examiner

FRACTIONATED SOYBEAN PROTEIN MATERIAL, PROCESSED SOYBEAN SUITABLE FOR THE MATERIAL, AND PROCESSES FOR PRODUCTION OF THE SOYBEAN PROTEIN MATERIAL AND THE PROCESSED SOYBEAN

This application is a U.S. national stage of International Application No. PCT/JP2006/310751 filed May 30, 2006.

TECHNICAL FIELD

The present invention relates to a fractionated soybean protein material, a processed soybean suitable for the material, and processes for production of the soybean protein material and the processed soybean. More particularly, the present invention relates to a fractionation technique for a soybean protein into proteins having characteristic properties (7S globulin, 11S globulin and a lipophilic protein).

BACKGROUND ART

Soybean protein has been widely utilized for improving physical properties of foods because of its peculiar gelling property, and at the same time, use of soybean protein as a highly nutritious health food material has been increased.

A storage protein of a soybean is precipitated at around pH 4.5, and therefore soybean protein can be relatively simply separated into an acid-soluble protein fraction mainly containing soluble components other than a storage protein and an acid-precipitable protein fraction mainly containing a storage protein. The acid-precipitable protein fraction is collected to obtain an isolated soybean protein, which has been currently widely used in the food industry.

Proteins constituting a soybean protein are classified into 2S globulin, 7S globulin, 11S globulin and 15S globulin based on sedimentation coefficient by ultracentrifuge analysis. Among them, 7S globulin and 11S globulin are the main constituent protein components of a globulin fraction. Herein, β-conglycinin and glycinin according to immunological nomenclature substantially correspond to 7S globulin and 11S globulin respectively.

Proteins constituting soybean protein are each different in physical properties such as viscosity, coagulation property and surface activity, and nutritional physiological functions.

For example, it has been reported that 7S globulin decrease neutral fat in blood (see Non-Patent Document 1). It has been believed that 11S globulin has a high gelling activity and governs the hardness and mouth feeling of a bean curd gel.

Thus, fractionation of soybean protein into fractions rich in these components enables physiological functions or physical properties peculiar to each protein component to greatly manifest, probably leading to creation of a characteristic material. Therefore, extension of the field utilizing soybean protein in the food industry can be expected.

As seen from FIG. 1 showing dissolution behavior of 7S globulin and 11S globulin for a pH, 7S globulin has a low solubility at about pH 4.8 and 11S globulin has a low solubility at from pH 4.5 to 6. Thus, it is expected that respective components with a high purity may be fractionated by first precipitating 11S globulin at about pH 6 and then further lowering pH to precipitate 7S globulin.

However, in fact, when soybean milk is adjusted to pH 6 and separated into an insoluble fraction and a water-soluble fraction and then, these fractions are subjected to SDS-polyacrylamide gel electrophoresis, the obtained electrophoresis patterns show that considerable amounts of 7S globulin and 11S globulin are mixed in both fractions.

For this reason, there is a problem that only a simple fractionation based on dissolution behavior of both globulins for a pH can not obtain their fractions with a high purity.

In order to overcome such a problem, some techniques for fractionation of 7S globulin and 11S globulin have been disclosed (see Non-Patent Document 2, Patent Documents 1 to 7 etc.).

On the other hand, it has been reported in recent years that an acid-precipitable soybean protein fraction comprises various proteins having high affinity for polar lipids which constitutes the membrane of a protein body, an oil body and the like including a cell membrane, in addition to 7S globulin and 11S globulin (see Non-Patent Document 3).

Considering such a report, the present inventors studied. As a result, they found that when sodium sulfate was added to low-denatured defatted soybean milk so as to be a 1 M concentration and the soybean milk was then adjusted to pH 4.5 with hydrochloric acid, 7S and 11S globulins transferred into an acid-soluble fraction and other various proteins transferred into an acid-precipitable fraction (see Non-Patent Document 4).

It was also found that the nitrogen amount of the acid-precipitable fraction accounted for about 30% of the total nitrogen amount in the defatted soybean milk, which was an unexpected large amount.

Further, it has been reported that an industrially produced isolated soybean protein contains about 35% of these various proteins, and it has been found that such a group of proteins influence the flavor of a conventional soybean protein material such as soybean milk or an isolated soybean protein (see Non-Patent Document 5).

The acid-precipitable fraction that is not rich in 7S globulin and 11S globulin comprises proteins having mainly a deduced molecular weight of 34 kDa, 24 kDa and 18 kDa based on SDS-polyacrylamide electrophoresis, lipoxygenase, γ-conglycinin and other many various proteins. Such a group of proteins have affinity for a polar lipid.

According to the above described findings, it is understood that the previous fractionation techniques (Non-Patent Document 2, Patent Documents 1 to 7) could not substantially attain fractionation of 7S globulin and 11S globulin with a high purity because it was not previously considered at all that lipophilic proteins account for a considerable proportion of an acid-precipitable soybean protein fraction.

Although Non-Patent Document 4 has shown a method for fractionation of 7S globulin, 11S globulin and a lipophilic protein with a high purity, said method needs use of a large amount of a reducing agent under a high ionic strength and thus needs a desalting step and a washing step. Therefore, said method is effective at the experimental level, but is not suitable for an industrial process.

Then, the present applicant developed a technique for fractionating a soybean protein into a soybean 7S globulin protein fraction with a high purity which has a low content rate of a lipophilic protein, and a soybean 11S globulin protein fraction (see Patent Documents 8 and 9). Said method was industrially excellent in that 7S globulin with a high purity could be fractionated. However, in order to obtain a soybean 11S globulin fraction with a high purity which has a decreased content rate of a lipophilic protein, a troublesome procedure was needed. Therefore there was room for improvement in said method.

In other words, development of a process for preparing a general isolated soybean protein or both of 7S globulin and 11S globulin with a low content rate of a lipophilic protein, but not a process for fractionating only 7S globulin with a high purity, is desired. In addition, a simple method which can fractionate each of 7S globulin, 11S globulin and a lipophilic protein with a high purity is desired.

REFERENCE DOCUMENTS

Non-Patent Document 1: Okita T et al., J. Nutr. Sci. Vitaminol., 27(4), 379-388, 1981
Non-Patent Document 2: Thanh, V. H, and Shibasaki, K., J. Agric. FoodChem., 24, 1117-1121, 1976
Non-Patent Document 3: Herman, Planta, 172, 336-345, 1987
Non-Patent Document 4: Samoto M et al., Biosci. Biotechnol. Biochem., 58(11), 2123-2125, 1994
Non-Patent Document 5: Samoto M et al., Biosci. Biotechnol. Biochem., 62(5), 935-940, 1998
Non-Patent Document 6: T. Nagano, et al., Relationship between rheological properties and conformational states of 7S globulin from soybeans at acidic pH, Food Hydrocolloids: Structures, Properties, and Functions, Plenum Press, New York, 1994
Patent Document 1: JP-A 55-124457
Patent Document 2: JP-A 48-56843
Patent Document 3: JP-A 49-31843
Patent Document 4: JP-A 58-36345
Patent Document 5: JP-A 61-187755
Patent Document 6: WO 00/58492
Patent Document 7: U.S. Pat. No. 6,171,640
Patent Document 8: WO 02/28198
Patent Document 9: WO 2004/43160

DISCLOSURE OF THE INVENTION

Problems to be Solved by the Invention

In view of the above described problems, an objective of the present invention is to provide a means for fractionating not only 7S globulin but also three protein fractions of 7S globulin, 11S globulin and a lipophilic protein with high efficiency and a high purity. A further objective of the present invention is to provide soybean milk and an isolated soybean protein which have a decreased content of a lipophilic protein. And, another object of the present invention is to provide such processes practicable at the food industrial level.

Means for Solving the Problems

In order to solve the above described problems, the present inventors intensively studied and, as a result, found that when a processed soybean was prepared by subjecting a low-denatured soybean containing protein and soybean curd refuse to a specific denaturation treatment and then soybean milk was extracted from the processed soybean as raw material, the soybean milk could be fractionated into 7S globulin, 11S globulin and a lipophilic protein with high efficiency and a high purity by a simple fractionation method, thereby the above described problems could be solved.

That is, the present inventors found that when a processed soybean is prepared by subjecting a soybean to a denaturation treatment under such a condition that 7S globulin and 11S globulin remain low-denatured and only a lipophilic protein is selectively denatured and then soybean milk is extracted from the processed soybean as raw material, 7S globulin and 11S globulin are mainly extracted, while extraction of a lipophilic protein is suppressed and a considerable amount of a lipophilic protein remains in soybean curd refuse as an insoluble fraction.

And, it was found that, by only adjusting the resulting soybean milk having a small amount of a lipophilic protein to a pH region at which a difference in solubility between 7S globulin and 11S globulin is greater, fractionation of both globulins with a high purity can be easily attained.

Further, it was found that, by adding water to the resulting soybean curd refuse followed by hot extraction, a lipophilic protein, which was previously difficult to separate from S7 globulin and 11S globulin, can be fractionated at a high purity. The present inventors examined the physiological action of the fractionated lipophilic protein, and as a result, obtained the finding that the lipophilic protein has a remarkable blood cholesterol-lowering activity as compared with a conventional isolated soybean protein and fractionated 7S globulin and 11S globulin.

Further, it was found that soybean milk and an isolated soybean protein which are obtained from the processed protein in which a lipophilic protein is selectively denatured are excellent in flavor as compared with those obtained by a conventional process.

Further, it was found that soybean curd refuse obtained from the processed soybean in which a lipophilic protein is selectively denatured contains a large amount of a lipophilic protein.

Further, a method for fractionation of soybean protein according to the present invention can be also applied to the case where a 7S globulin-deficient soybean is used and two fractions of 11S globulin and a lipophilic protein are prepared.

That is, the present invention provides:
1. A processed soybean comprising a protein component and a soybean curd refuse component, wherein PDI is not less than 40 and less than 80 and, among contained proteins, a lipophilic protein is selectively water-insolubilized;
2. The processed soybean according to the above 1, wherein a selective water-insolubilization index (LP/MSP) is not more than 45%;
3. The processed soybean according to the above 1, wherein a selective water-insolubilization index (LP/MSP) is not more than 35%;
4. The processed soybean according to the above 1, which is used for fractionation of one or more acid-precipitable soybean proteins selected from 7S globulin, 11S globulin and a lipophilic protein;
5. A process for producing the processed soybean according to the above 1, which comprises impregnating soybeans comprising a protein component and a soybean curd refuse component as raw material with an equal or less weight of a polar alcohol solution;
6. The process for producing the processed soybean according to the above 5, which comprises a step of impregnation with a polar alcohol solution and a step of a warming treatment at a product temperature of 30 to 95° C.;
7. A process for producing the processed soybean according to the above 2, which comprises subjecting soybeans comprising a protein component and a soybean curd refuse component as raw material to a heating treatment;
8. Use of the processed soybean according to the above 1, for production of a fractionated soybean protein in which at least an acid-precipitable soybean protein selected from the group consisting of 7S globulin, 11S globulin and a lipophilic protein is concentrated;
9. A process for producing a fractionated soybean protein, which comprises preparing soybean milk or soybean curd refuse as raw material from the processed soybean according to the above 1, and then collecting, from the soybean milk or soybean curd refuse, a fraction in which at least an acid-precipitable soybean protein selected from the group consisting of 7S globulin, 11S globulin and a lipophilic protein is concentrated;

10. A soybean 11S globulin protein which is obtained by fractionation of soybean milk prepared from the processed soybean according to the above 1;

11. A process for producing a soybean 11S globulin protein, which comprises adjusting soybean milk prepared from the processed soybean according to the above 1 to pH 5.2 to 6.4, and then collecting an insoluble fraction;

12. A soybean 7S globulin protein which is obtained by fractionation of soybean milk prepared from the processed soybean according to the above 1;

13. A process for producing a soybean 7S globulin protein, which comprises adjusting soybean milk prepared from the processed soybean according to claim 1 to pH 5.2 to 6.4, separating an insoluble fraction to obtain a water-soluble fraction, adjusting the water-soluble fraction to pH 4 to 5.5, and then collecting an insoluble fraction produced;

14. A process for producing a soybean 7S globulin protein, which comprises adjusting the water-soluble fraction as defined in the above 13 to pH 4 to 5.5, heating the fraction at 40 to 65° C., adjusting the fraction to pH 5.3 to 5.7, separating an insoluble fraction produced to obtain a water-soluble fraction, adjusting the water-soluble fraction to pH 4 to 5, and then collecting an insoluble fraction produced;

15. A process for producing a soybean 7S globulin protein, which comprises adjusting soybean milk prepared from the processed soybean according to the above 1 to pH 4 to 5.5, heating the soybean milk at 40 to 65° C., adjusting the soybean milk to pH 5.3 to 5.7, separating an insoluble fraction produced to obtain a water-soluble fraction, adjusting the water-soluble fraction to pH 4 to 5, and then collecting an insoluble fraction produced;

16. A non-7S/11S-acid-precipitable soybean protein which is obtained by fractionation of soybean curd refuse prepared from the processed soybean according to the above 1, and wherein the content of an oil component extracted with a mixture of chloroform and methanol at a volume ratio of 2:1 as a solvent is not less than 7%;

17. The non-7S/11S-acid-precipitable soybean protein according to the above 16, which has a LCI value of not less than 60%;

18. A process for producing a non-7S/11S-acid-precipitable soybean protein, which comprises adding water to soybean curd refuse prepared from the processed soybean according to the above 1, subjecting the mixture to hot extraction, and then recovering an extract;

19. The process for producing a non-7S/11S-acid-precipitable soybean protein according to the above 18, which comprises subjecting the extract to acid-precipitation, and then collecting an insoluble fraction produced;

20. A non-7S/11S-acid-precipitable soybean protein which is obtained by fractionation of soybean milk prepared from the processed soybean according to the above 1, and wherein the content of an oil component extracted with a mixture of chloroform and methanol at a volume ratio of 2:1 as a solvent is not less than 7%;

21. The non-7S/11S-acid-precipitable soybean protein according to the above 20, which has a LCI value of not less than 60%;

22. A process for producing a non-7S/11S-acid-precipitable soybean protein, which comprises collecting the insoluble fraction produced by adjustment to pH 5.3 to 5.7 as defined in the above 14;

23. Soybean milk which is prepared from the processed soybean according to the above 5 as raw material;

24. A process for producing soybean milk, which comprises extracting the processed soybean according to the above 5 with water, and then collecting a water-soluble fraction;

25. Soybean curd refuse which is prepared from the processed soybean according to the above 5 as raw material;

26. A process for producing soybean curd refuse, which comprises extracting the processed soybean according to the above 5 with water, and then collecting an insoluble fraction;

27. An isolated soybean protein which is obtained using, as raw material, soybean milk prepared from the processed soybean according to the above 5;

28. The isolated soybean protein according to the above 27, which has a LCI value of not more than 38%;

29. A method for fractionating a soybean protein, which comprises the following steps:

(1) adding water to the processed soybean according to claim 1, and separating the mixture into soybean milk and soybean curd refuse;

(2) adjusting the soybean milk obtained in the step (1) to pH 5.2 to 6.4, and separating a water-soluble fraction to obtain a soybean 11S globulin protein as an insoluble fraction;

(3) adjusting the water-soluble fraction obtained in the step (2) to pH 4 to 5.5, heating the fraction at 40 to 65° C., and then adjusting the fraction to pH 5.3 to 5.7, and separating a water-soluble fraction produced to obtain a non-7S/11S-acid-precipitable soybean protein as an insoluble fraction; and (4) adjusting the water-soluble fraction separated after adjustment to pH 5.3 to 5.7 in the step (3) to pH 4 to 5 to obtain a soybean 7S globulin protein as an insoluble fraction;

30. The processed soybean according to the above 1, which is a 7S globulin-deficient soybean;

31. The process for producing a fractionated soybean protein according to the above 9, wherein the soybean is a 7S globulin-deficient soybean;

32. A process for producing a non-7S/11S-acid-precipitable soybean protein, which comprises adjusting soybean milk prepared from the processed soybean according to the above 30 to pH 5.2 to 6.4, separating an insoluble fraction to obtain a water-soluble fraction, adjusting the water-soluble fraction to pH 4 to 5, and then collecting an insoluble fraction produced;

33. A method for fractionating a soybean protein, which comprises the following steps:

(1) adding water to the processed soybean according to claim 30, and separating the mixture into soybean milk and soybean curd refuse;

(2) adjusting the soybean milk obtained in the step (1) to pH 5.2 to 6.4, and separating a water-soluble fraction to obtain a soybean 11S globulin protein as an insoluble fraction; and (3) adjusting the water-soluble fraction obtained in the step (2) to pH 4 to 5, separating a water-soluble fraction produced to obtain a non-7S/11S-acid-precipitable soybean protein as an insoluble fraction;

34. A composition for lowering blood cholesterol, comprising the non-7S/11S-acid-precipitable soybean protein according to the above 16;

35. A composition for lowering blood cholesterol, comprising the non-7S/11S-acid precipitable soybean protein according to the above 20;
36. Use of the non-7S/11S-acid-precipitable soybean protein according to the above 16, for preparation of a composition for lowering blood cholesterol;
37. Use of the non-7S/11S-acid-precipitable soybean protein according to the above 20, for preparation of a composition for lowering blood cholesterol.

Effect of the Invention

According to a simple method of the present invention suitable for an effective production process, it is possible to fractionate a soybean protein into three fractions of 7S globulin, 11S globulin and a lipophilic protein with a high purity. Since said fractionation method is a method mainly comprising adjustment of pH without addition of a salt unlike a conventional fractionation method comprising addition of a salt, it does not need a dilution step and a desalting step for realizing a low ion concentration environment necessary for recovering a protein as a precipitate. Therefore, said fractionation method is an excellent method in which an operation for fractionation is simplified.

Further, it is possible to provide soybean milk and an isolated soybean protein having an excellent flavor and containing little lipophilic protein from the processed soybean of the present invention.

Since soybean milk, an isolated soybean protein, a soybean 11S protein, a soybean 7S protein, a soybean curd refuse and a non-7S/11S-acid-precipitable soybean protein which are obtained from the processed soybean of the present invention as raw material exhibit a pleasant, refreshing and extremely better flavor as compared with conventional soybean protein materials, they have increased utility value as a food material.

Further, since the lipophilic protein of the present invention has a blood cholesterol-lowering effect greater than that of a conventional isolated soybean protein, the non-7S/11S-acid-precipitable soybean protein which is a novel material has high utility value as a health functional material.

BEST MODE FOR CARRYING OUT THE INVENTION

First, terms as used in the present invention will be explained.

The "7S globulin" is also referred to as β-conglycinin, and is a glycoprotein which is generally composed of three kinds of subunits (α', α, β), and any of subunits may be lacked. These subunits are randomly combined to form a trimer. 7S globulin has an isoelectric point of around pH 4.8 and a molecular weight of about 170,000. Hereinafter, 7S globulin is simply abbreviated as "7S" in some cases.

The "soybean 7S protein" refers to a soybean protein material having an increased purity of 7S.

The "11S globulin" is also referred to as glycinin, and is a dodecamer formed of 6 molecules wherein a molecule consists of an acidic subunit and a basic subunit bound to each other via a disulfide bond. The molecular weight of 11S globulin is about 360,000. Hereinafter, 11S globulin is simply abbreviated as "11S" in some cases.

The "soybean 11S protein" refers to a soybean protein material having an increased purity of 11S.

Both of 7S and 11S are acid-precipitable soybean proteins, and are main storage proteins which are stored in a soybean protein body.

The "acid-precipitable soybean protein" as used herein refers to a protein that is precipitated when the pH of a soybean protein solution such as defatted soybean milk is adjusted to an acidic side (pH 4 to 6), among soybean proteins. Therefore, for example, proteins comprised in an isolated soybean protein correspond to the acid-precipitable soybean protein, and proteins comprised in whey which are not acid-precipitated in the production of an isolated soybean protein are not included in the acid-precipitable soybean protein.

7S and 11S, depending on the varieties of soybeans, account for about 70% of all soybean proteins comprised in a conventional isolated soybean protein (SPI) or the like, as determined by measuring peak areas in SDS electrophoresis with a densitometry after Coomassie Brilliant Blue (CBB) staining.

The total content of 7S and 11S in a soybean protein can be determined by (Method 1) and (Method 2) as described below.

Hereinafter, 7S and 11S are collectively abbreviated as "MSP" in some cases.

The "lipophilic protein" refers to a group of minor acid-precipitable soybean proteins other than 7S and 11S among acid-precipitable soybean proteins of a soybean, and is accompanied by a lot of polar lipids such as lecithin and glycolipid. Hereinafter, the lipophilic protein is simply abbreviated as "LP" in some cases.

The LP comprises proteins mainly having a presumed molecular weight of 34 kDa, 24 kDa and 18 kDa based on SDS-polyacrylamide electrophoresis, lipoxygenase, γ-conglycinin, and many other various proteins (see FIG. 2, lane 3).

As seen from FIG. 2, LP is difficult to stain in SDS electrophoresis as compared with 7S and 11S, so that the actual entity has not previously been recognized clearly. For this reason, bands on SDS electrophoresis described as a single band of 7S and 11S in previous literatures actually comprise a considerable amount of LP, in many cases.

Since LP is a mixture of various proteins, it is difficult to specify all of respective proteins. However, LP can be fractionated based on dissolution behavior by (Method 1) and (Method 2) as described below.

The "non-7S/11S-acid-precipitable soybean protein" refers to a soybean protein material having an increased purity of LP. Hereinafter, the non-7S/11S-acid-precipitable soybean protein is simply abbreviated as "LP-SPI" in some cases.

The "PDI" is an abbreviation of "protein dispersibility index", and an index obtained by measuring a dispersible protein contained in a soybean product under a constant condition by an AOCS official method (Ba10-65). In contrast with a method comprising mild stirring, for example, for obtaining "NSI" (AOCS official method Ba11-65), the AOCS official method (Ba10-65) comprises vigorous stirring, and generally leads to a higher numerical value result. Herein, water was added to soybeans, and the mixture was stirred with a mixer and then centrifuged to obtain a supernatant. Then, the amount of nitrogen contained in the supernatant was measured, and the proportion of the supernatant nitrogen amount to the soybean nitrogen amount was calculated. As a numerical value obtained is higher, the protein solubility of a soybean is higher. When a soybean protein becomes hardly soluble because of heat treatment or the like, a PDI value is decreased.

The "selective water-insolubilization index" is an index indicating numerically the extent of selective water-insolubilization of LP contained in the processed soybean of the present invention, and is expressed as the ratio "LP/MSP"

wherein LP and MSP are respectively the LP nitrogen amount (%) and the MSP nitrogen amount (%) to the total nitrogen amount contained in a water-soluble fraction of a soybean.

Then, embodiments of the present invention will be explained in detail.

The first aspect of the present invention is a processed soybean comprising a protein component and a soybean curd refuse component, wherein PDI is not less than 40 and less than 80 and, among contained proteins, a lipophilic protein is selectively water-insolubilized. Said processed soybean can be used as soybean raw material for fractionation of one or more acid-precipitable soybean proteins selected from 7S globulin, 11S globulin and a lipophilic protein, thereby these proteins can be efficiently fractionated without a troublesome operation to obtain various characteristic soybean protein materials.

[Soybean as Raw Material]

Soybeans used as raw material in the present invention contain at least a protein component and a soybean curd refuse component, and the varieties of soybeans are not particularly limited because there is no soybean variety which lacks LP or comprises an extremely decreased amount of LP as long as it has an oil body storing lipids. Any variety of soybeans can be applied to the present invention.

A soybean rich in 7S and a soybean rich in 11S produced by breeding technique or genetic engineering technique, and a soybean in which a particular component is altered such as a lipoxygenase-deficient variety can be also used as raw material. Particularly, in the case where a soybean rich in 11S, that is, a 7S globulin-deficient soybean is used as raw material, the selective water-insolubilization technique of LP of the present invention can be utilized upon fractionation of 11S and LP which are the main acid-precipitable soybean proteins contained in the soybean.

However, since LP comprises a lot of proteins derived from oil bodies, it is preferable that a soybean variety having a low lipid content is used in order to obtain 7S and 11S efficiently. In addition, the hypocotyl or outer skin of a soybean as raw material may be removed or not removed.

In the case where various soybean protein materials such as an isolated soybean protein, a soybean 7S protein, a soybean 11S protein and the like are prepared using the processed soybean of the present invention as raw material, it is preferable that defatted soybeans as raw material are used because lipids contained in soybeans influence the purity of a protein obtained. As the defatted soybean, a defatted soybean obtained by defatting a soybean with an organic solvent such as hexane, and a defatted soybean obtained by compressing a soybean to decrease the oil content can be used.

The form of a soybean as raw material is not particularly limited. Preferably a ground soybean is used, and suitably a soybean powder having a maximum particle diameter of not more than 500 µm, more preferably not more than 300 µm, further preferably not more than 100 µm is used.

In addition, it is desirable that denaturation of proteins contained in a raw material soybean has not extremely proceeded before a processing treatment in the present invention, and a soybean having PDI of not less than 60 is preferable wherein PDI indicates a protein extraction rate. The moisture of the soybean is preferably 2 to 15%, more preferably 5 to 10%.

[Processed Soybean]

The processed soybean of the present invention in which PDI is not less than 40 and less than 80 and a lipophilic protein among contained proteins is selectively water-insolubilized is characterized in that 7S and 11S among acid-precipitable soybean proteins are selectively in the low-denatured state.

In other words, the processed soybean of the present invention is a processed soybean characterized by so-called selective extraction of a protein when extracted with water, that is, suppressed extraction of water-insolubilized LP and selective extraction of low-denatured 7S and 11S. If preparation of a similar processed soybean is tried by a heating treatment that has been conventionally performed to inactivate lipoxygenase or by washing with a large amount of ethanol, almost all proteins including 7S and 11S are water-insolubilized and thus the insolubilization is non-selective.

When a processed soybean having a great thermal history and PDI of less than 40 is used, a smell derived from a soybean, a roasted smell, a burnt smell and the like occur because of heat, being not preferable from a viewpoint of a quality. In such a processed soybean, non-selective insolubilization of a protein occurs, that is, not only LP but also 7S and 11S are insolubilized, so that the extraction rate of a protein from the processed soybean is decreased and, at the same time, it is difficult to extract selectively 7S and 11S.

Whether a processed soybean has a characteristic that only LP is selectively water-insolubilized or not can not be determined by only PDI, which is a dissolution index of a protein. Whether a processed soybean has such a characteristic or not can be determined by a selective water-insolubilization index (LP/MSP).

When LP/MSP is not more than 45%, it can be said that LP is selectively water-insolubilized. A processed soybean having LP/MSP of not more than 45% is sufficient to obtain a fraction of a soybean protein, and LP/MSP is more preferably not more than 35%, further preferably not more than 30%.

LP/MSP may be not more than 28%, and further may be not more than 23%.

As described above, whether only LP contained in a processed soybean is selectively water-insolubilized or not can not be determined by analyzing directly a processed soybean itself, but it can be determined by analyzing LP/MSP of a water-soluble fraction obtained by water-extraction from the processed soybean, that is, soybean milk.

LP/MSP can be specifically calculated by obtaining a water-soluble fraction from a processed protein by the following Method 1, fractionating the fraction into a LP fraction and a MSP fraction by the following Method 2, and then obtaining the nitrogen amount of each fraction by a Kjeldahl method.

<Method of Calculating Selective Water-Insolubilization Index (LP/MSP)>

(Method 1)

A processed soybean sample (in the case of a whole fat soybean, it is defatted with hexane to less than 1.5% of an oil content in advance) is ground, and is adjusted to a particle size of 60 mesh pass. To 1 part by weight of the soybean is added 7 parts by weight of water. The mixture is adjusted to pH 7.5 with sodium hydroxide, stirred at room temperature for 30 minutes, and then centrifuged at 1000 G for 10 minutes to be separated into a water-soluble fraction A and an insoluble fraction A. Further, 5 parts by weight of water is added to the insoluble fraction A, and stirred at room temperature for 30 minutes. The mixture is centrifuged at 1000 G for 10 minutes to be separated into a water-soluble fraction B and an insoluble fraction B. The water-soluble fractions A and B are mixed to obtain a water-soluble fraction. The insoluble fractions A and B are mixed to obtain an insoluble fraction. Operations from water addition to separation are performed at 10° C. to 25° C. Stirring is performed with a propeller (350 rpm).

(Method 2)

The water-soluble fraction obtained by Method 1 is adjusted to pH 4.5 by addition of hydrochloric acid. The mixture is centrifuged at 1000 G for 10 minutes and an insoluble fraction C is collected. Further, to the insoluble fraction C is added a 1M $Na_2SO_4$ (containing 20 mM mercaptoethanol) solution in an amount of 5 times the weight of the sample processed soybean used in Method 1. The mixture is stirred well, and centrifuged at 10000 G for 20 minutes to be separated into a water-soluble fraction D and an insoluble fraction D. The insoluble fraction D is subjected to the same operation as described above to be separated into a water-soluble fraction E and an insoluble fraction E. The insoluble fractions D and E are combined to obtain a LP fraction, and the water-soluble fractions D and E are combined to obtain a 7S and 11S fraction (MSP fraction). An operation temperature is 10° C. to 25° C. The nitrogen amounts of the LP fraction and the MSP fraction thus obtained are measured by a Kjeldahl method, and the ratio between them is determined.

<Preparation of Processed Soybean>

A method for obtaining a processed soybean in which LP is selectively water-insolubilized is not particularly limited as long as the selective water-insolubilization index (LP/MSP) of the obtained processed soybean is not more than 45%. For example, a known method for protein denaturation, such as heat denaturation, denaturation with a protein denaturation agent such as an alcohol and the like, may be used and a person skilled in the art can appropriately select a processing method and the condition thereof.

(Heat Denaturation Treatment)

When heat denaturation is utilized as one aspect of a denaturation method, a method for heating a soybean includes, but not limited to, a dry heating method using a roasting device, a hot air heating device, a microwave heating device or the like, and a wet heating method using a humidifying and heating device, a steaming device, a steam heating device or the like. However, when a soybean soaked in water is heated, proteins are extracted. Thus, it is better to avoid heating a soybean soaked in water.

As an example, a method which comprises enclosing a soybean in a sealed tank, and heating the inside of a jacket covering the outside of the sealed tank under an atmosphere of a relative humidity of not lower than 90% so that a product temperature becomes about 70 to about 95° C. can be adopted.

Heating conditions such as temperature and time are not particularly limited as long as they allow LP to be selectively insolubilized. The heating temperature is usually set to be a product temperature of 60 to 95° C., and the heating time is suitably between 1 minute and 10 hours.

(Alcohol Denaturation Treatment)

When alcohol denaturation is utilized as another aspect of a denaturation method, a preferable method comprises adding an equal weight or less, preferably 2 to 100 parts by weight, more preferably 8 to 20 parts by weight, further preferably 10 to 15 parts by weight of a polar alcohol solution to 100 parts by weight of a raw material soybean comprising a protein component and a soybean curd refuse component, thereby impregnating the raw material soybean with the polar alcohol solution. According to said method, it is easy to make LP/MSP not more than 30%, and selective water-insolubilization of only LP can be attained more efficiently.

Said method is entirely different in an idea from a method comprising immersing a soybean in a many-fold amount of an alcohol to obtain a suspension, thereby washing nonprotein components of a soybean such as saccharides, for example, a conventional process for producing a concentrated soybean protein using alcohol washing. Said method comprises adding an equal weight or less of a polar solvent solution to a soybean, thereby impregnating the soybean with the solvent. In this case, the state of a soybean mixed with a solvent typically becomes a wetted powder state.

However, when the addition amount of a polar solvent is less than 2% by weight of the amount of a soybean, selective water-insolubilization of LP is insufficient, and then the effect of suppressing extraction of LP upon water extraction tends to be insufficient. Conversely, when the addition amount of a polar solvent is more than an equal weight of the soybean amount, non-selective water-insolubilization wherein 7S and 11S together with LP are water-insolubilized easily occurs, and even extraction of 7S and 11S becomes insufficient.

Examples of a suitable polar solvent used for promoting selective water-insolubilization of LP include polar alcohol solutions (methanol, ethanol, propanol, isopropanol etc.). Particularly, it is preferable to use a solution of ethanol in water which is frequently used in the food industry. As water, pure water may be used, or an aqueous acid solution (an aqueous hydrochloric acid solution, an aqueous carbonic acid solution, an aqueous citric acid solution etc.), an aqueous alkali solution (a sodium hydroxide solution, sodium bicarbonate etc.) or the like may be used.

The concentration of a polar solvent solution is preferably 5 to 100%, more preferably 50 to 80%. When the concentration of a polar solvent solution is too low or too high, water-insolubilization of LP due to denaturation is insufficient.

Addition of a polar solvent solution to a soybean can be carried out, for example, by spraying the solvent solution to soybean powder or by adding dropwise the solvent solution to a soybean, but not be particularly limited. For mixing after addition of a polar solvent solution, for example, a stirring machine such as a kneader, a high speed stirring machine or the like can be used.

Furthermore, it is preferable that a warming treatment is used in combination with the above-described alcohol impregnation treatment. The warming temperature is preferably 30 to 95° C., more preferably 40 to 90° C. of a product temperature of a soybean. The warming time is preferably 5 to 100 minutes, more preferably 10 to 60 minutes.

When the impregnation treatment with a polar solvent and the warming treatment are used in combination, the order of performing these treatments is not particularly limited. However, it is preferable that a polar solvent is added and mixed before a warming treatment, or a warming treatment is performed while a polar solvent is added and mixed.

A combination use of the impregnation treatment with a polar solvent and the warming treatment allows efficient selective water-insolubilize of only LP contained in a soybean even if a relatively low temperature treatment is used. In addition, when the impregnation treatment with a polar solvent and the warming treatment are used in combination, generation of a color and a smell due to heating is suppressed, thereby the flavor of a processed soybean, or a product prepared from a processed soybean as raw material can be improved.

Furthermore, the addition amount of a polar solvent can be decreased, and therefore, a step of removing a polar solvent after treatment becomes extremely easy as compared with a conventional alcohol washing method, which is advantageous to establishment of an efficient production process.

Almost all of a polar solvent remaining in a processed soybean can be vaporized by the warming treatment, which can be directly subjected to an extraction step. However, if it is desired that the remaining amount of a polar solvent is further decreased, a further warming treatment can be performed at a product temperature of 40 to 60° C. under reduced pressure (about −10 mmHg) for 10 to 60 minutes to vaporize completely the polar solvent, thereby the weight of a soybean can be returned to approximately the same weight before addition of the polar solvent.

The vaporized polar solvent can be recovered by distillation and then can be reused, which is advantageous from a viewpoint of a production process.

The inventions described below have the common technical feature that the processed soybean in which LP is selectively water-insolubilized is used as raw material for fractionation of one or more acid-precipitable soybean proteins selected from 7S, 11S and LP.

In other words, the inventions comprise that soybean milk or soybean curd refuse prepared from the processed soybean is used as raw material, a fraction in which at least an acid-precipitable soybean protein selected from the group consisting of 7S globulin, 11S globulin and a lipophilic protein is concentrated is collected, and thereby a fractionated soybean protein is obtained.

(1) Soybean Milk

The soybean milk of the present invention is prepared from the processed soybean as raw material. Preferably, the soybean milk of the present invention is prepared from the processed soybean obtained by the above-described alcohol denaturation treatment as raw material.

A process for producing the soybean milk of the present invention is not particularly limited as long as the processed soybean is used as raw material. For example, the raw material is extracted with an aqueous solvent such as water or an aqueous alkali solution, and separated into soybean milk and soybean curd refuse by centrifugation, and then a soluble fraction is collected to obtain the soybean milk of the present invention.

The addition amount of the aqueous solvent is preferably 6 to 12 times, more preferably 7 to 9 times the weight of the processed soybean. When the addition amount of the aqueous solvent is too small, the mixture has an increased viscosity, and when the addition amount of the aqueous solvent is too large, the mixture becomes a dilute solution, thereby the recovery efficiency of the soybean milk is decreased.

The temperature for extraction is preferably about 4 to about 50° C., more preferably about 10 to about 30° C. When the temperature is too high, LP is easily dissolved. When the temperature is too low, an extraction efficiency is decreased.

Soybean curd refuse which is insoluble at around neutral pH 6 to 9 is removed from the resulting extract by centrifugation or the like. For the purpose of increasing the recovery amount of soybean milk, to the resulting soybean curd refuse may be further added a 4 to 6-fold weight of water followed by extraction, and such a procedure may be repeated.

The soybean milk prepared from the processed soybean of the present invention as raw material as described above may be commercialized as it is, or may be further processed into concentrated soybean milk or powdery soybean milk, or may be processed into modified soybean milk by adding suitable ingredients.

The soybean milk thus obtained has an extremely characteristic protein composition different from that of conventional soybean milk. The characteristic protein composition of the soybean milk comprises a low LP content, and LP/MSP of not more than 45%, preferably not more than 35%, further preferably not more than 30%, further preferably not more than 28%, most preferably not more than 23%.

The soybean milk of the present invention can be used in production of a fractionated soybean protein as described below.

In contrast, soybean milk prepared by a conventional process or soybean milk extracted from a soybean in which proteins are nonselectively insolubilized has a LP/MSP ratio of more than 45% (see Table 1). In this case, it is difficult to fractionate soybean milk into a soybean 7S globulin protein and a soybean 11S globulin protein by a simple means of only pH adjustment, and it is difficult for the resulting various soybean protein materials to have a good flavor and a good color tone together.

(2) Isolated Soybean Protein

The isolated soybean protein of the present invention is characterized in that soybean milk prepared from the processed soybean of the present invention is used as raw material, and can be also produced by a conventionally used known process except for using such soybean milk as raw material.

Typically, an acid (hydrochloric acid, sulfuric acid etc.) is added to the soybean milk of the present invention to make the pH of the soybean milk acidic. The pH of the soybean milk may be adjusted to around the isoelectric point of a soybean protein, preferably pH 4.2 to 5.2. Among soybean proteins, an acid-precipitable soybean protein is insolubilized in said pH range to be precipitated. The precipitates are collected by centrifugation, and then neutralized by addition of an aqueous alkali such as sodium hydroxide to prepare a neutralized solution of a soybean protein, thereby an isolated soybean protein is obtained. After the isolated soybean protein thus obtained is optionally sterilized and dried, the isolated soybean protein in powder form may be used as it is, or formulated together with suitable pharmaceutical raw materials into a preparation, and then can be used as an isolated soybean protein in conventional various foods. As an alternative to the above-described method comprising an acid precipitation step, the isolated soybean protein can be obtained by washing the defatted soybean of the present invention with an acid, followed by extraction with water, as described in International Publication WO 2004/13170.

The isolated soybean protein thus obtained is characterized by more excellent flavor than that of a conventional isolated soybean, probably because the isolated soybean protein thus obtained has a crude protein content of not less than 90% by weight and has a low LP content.

Then, a method of measuring the content of LP in an isolated soybean protein will be explained.

Since an isolated soybean protein provided as a soybean protein material is generally heat-sterilized in the final productization step, 7S and 11S together with LP contained in the isolated soybean protein are denatured by heat. For this reason, it is difficult to fractionate the commercialized isolated soybean protein into a 7S, 11S fraction and a LP fraction and then measure the LP content by the above-described Methods 1 and 2.

In the case of a SDS-polyacrylamide gel electrophoresis method (SDS-PAGE) which is a general method of measuring a protein composition, it is difficult to satin LP with CBB, and therefore it is also difficult to measure the precise LP amount by said method.

Thus, the following method which comprises easily selecting the main proteins contained in 7S, 11S and LP proteins, determining a staining ratio among them, and estimating the LP content from the ratio can be adopted.

Said method can be applied not only to an isolated soybean protein but also to various fractionated soybean proteins such as a soybean 7S protein, a soybean 11S protein and LP-SPI.

[Method of Estimating LP Content]

(a) As the main proteins in respective proteins, an α subunit and an α' subunit (α+α') are selected for 7S, an acidic subunit (AS) is selected for 11S, and a 34 kDa protein and lipoxygenase (P34+Lx) are selected for LP. Then, a staining ratio among the selected proteins on SDS-PAGE is determined. Electrophoresis can be performed under the condition shown in Table 1.

(b) X(%)=(P34+Lx)/{(P34+Lx)+(α+α')+AS}×100(%) is calculated.

(c) Since the LP content of an isolated soybean protein prepared from a low-denatured defatted soybean is about 38% as measured by the fractionation methods of the above-described Methods 1 and 2 before heat-sterilization, (P34+Lx) is multiplied by a correction coefficient k*=6 so that X becomes 38(%).

(d) That is, an estimated LP content (Lipophilic Proteins Content Index, hereinafter abbreviated as "LCI") is calculated by the equation below.

TABLE 1

| | |
|---|---|
| Application amount: | 10 μl of a protein 0.1% sample solution per well |
| Well width: | 5 mm |
| Well volume: | 30 μl |
| Staining solution: | Coomassie Brilliant Blue (CBB) 1 g, methanol 500 ml, glacial acetic acid 70 ml (after CBB is completely dissolved in methanol, acetic acid and water are added to 1 L) |
| Staining time: | 15 hours |
| Discoloration time: | 6 hours |
| Densitometer: | GS-710 Calibrated Imaging Densitometer/Quantity One Software Ver.4.2.3 (Bio Rad Japan Co. Ltd) Scanning width: 5.3 mm, Sensitivity: 30 |

(Mathematical Formula 1)

$$LCI(\%) = \frac{k^* \times (P34 + Lx)}{k^* \times (P34 + Lx) + (\alpha + \alpha') + AS} \times 100$$

K*: Correction coefficient (6)
P34: LP main component, 34 kDa protein
Lx: LP main component, lipoxygenase
α: 7S main component, α subunit
α': 7S main component, α' subunit
AS: 11S main component, acidic subunit The isolated soybean protein obtained by the present invention has LCI of not more than 38%, preferably not more than 35%, more preferably not more than 30%, further preferably not more than 25%. When LCI exceeds 38%, such LCI value is close to the LCI value of an isolated soybean protein obtained by a conventional process, and therefore its quality is not different from a conventional isolated soybean protein's quality. On the other hand, as a LCI value is smaller, a flavor is more excellent.

(3) Soybean 11S Protein and Soybean 7S Protein

For fractionating an acid-precipitable soybean protein into 11S and 7S, a variety of methods have been tried as described in Background Art. The soybean 11S protein and the soybean 7S protein of the present invention are characterized in that both of them are obtained by fractionating soybean milk prepared from the processed soybean of the present invention.

Thereby, 7S and 11S can be separated into fractions each of which contains a high purity of each protein by a simple means without using a conventional complicated means to produce fractionated soybean proteins (soybean 7S protein, soybean 11S protein).

With regard to a method for fractionation of 7S and 11S, as long as the processed soybean of the present invention is used as raw material, any of known methods as described above in Background Art can produce a soybean 11S protein with a high purity and a low LP content. Therefore, a person skilled in the art can appropriately determine which fractionation method to select upon construction of a production process. However, particularly, the following method is simpler and preferable.

[Preparation Example of Soybean 11S Protein]

Regarding the soybean 11S protein of the present invention, the soybean milk of the present invention is adjusted to a specific pH, and a produced insoluble fraction is collected and optionally neutralized, sterilized and dried, and then used as it is in powder form or formulated together with suitable pharmaceutical raw materials into a preparation, thereby the fractionated soybean protein material with a high purity can be obtained efficiently.

The pH is adjusted with an acid (any kind of an acid can be used) to preferably to 5.2 to 6.4, more preferably to 5.7 to 6.2.

The electrophoresis pattern of the obtained fraction shows a low LP content as the electrophoresis pattern of the soybean milk of the present invention (see FIG. 4), and the flavor of the fraction is excellent.

When the above-described method is used, the soybean milk may be adjusted to the above-described pH range after addition of a reducing agent such as sodium sulfite. Thereby, separability is further improved. In the case of separation of 11S by a conventional method, a reducing agent is usually added at about 10 mM. However, in the case of the soybean milk of the present invention, addition of about 1 mM of a reducing agent is enough to lead to good separation.

Another example of a fractionation method includes a method comprising precipitation of 11S by cooling which is a conventional 11S separation method (see Non-Patent Documents 2 and 6), and such a method may be utilized. That is, a reducing agent is added to the soybean milk of the present invention, the soybean milk is adjusted to pH 6.1 to 6.5, cooled to 4 to 6° C. and then allowed to stand for half a day, and produced precipitates are collected, thereby 11S globulin is recovered. For separation of 11S, a reducing agent is usually added at 10 mM. However, in the case of using the soybean milk of the present invention, addition of about 1 mM of a reducing agent is enough to lead to good separation.

Since the soybean 11S protein thus obtained has such a high purity of 11S as not lower than 75% by weight, preferably not lower than 85% by weight, more preferably not lower than 90% by weight, it is possible to make use of the property peculiar to 11S by using the soybean 11S protein. Since 11S has a low viscosity and has a great gel strength due to heating, the soybean 11S protein can be used, for example, as a gelling agent or as a substitute for an egg white. In addition, since hard bean curd is obtained by using the soybean 11S protein, the soybean 11S protein can be used for imparting hardness to bean curd.

In addition, the soybean 11S protein has a LCI value of not more than 30%, more preferably not more than 25%, further preferably not more than 20%, and an extremely low LP content, and is excellent in flavor.

[Preparation Example of Soybean 7S Protein]

Regarding the soybean 7S protein of the present invention, the pH of a water-soluble fraction solution obtained after fractionation of the above described 11S is adjusted with an acid to 4 to 5.5, preferably 4.3 to 4.8, a produced insoluble fraction is collected and optionally neutralized or not, sterilized and dried, and then used as it is in powder form or formulated together with suitable pharmaceutical raw materials into a preparation, thereby the fractionated soybean protein material can be obtained. In this case, the purity of 7S in the soybean 7S protein is at least not lower than 38%, preferably not lower than 40%, more preferably not lower than 50%, further preferably not lower than 60%.

In order to further increase the purification degree of 7S, LP can be removed as an insoluble fraction before the above-described step.

That is, a water-soluble fraction obtained upon preparation of the soybean 11S protein of the present invention is adjusted to pH 4 to 5.5, preferably pH 4.8 to 5.2, heated at 40 to 65° C., and then adjusted to pH 5.3 to 5.7, thereby proteins other than 7S (mainly LP) become insoluble and said proteins can be removed as an insoluble fraction. When it is not necessary to recover 7S and 11S from soybean milk at the same time, using the soybean milk of the present invention in place of the water-soluble fraction, only 7S can be directly fractionated from the soybean milk, and 11S and LP can be removed as an insoluble fraction.

Then, the pH of a water-soluble fraction after removal of the insoluble fraction is adjusted with an acid to 4 to 5, preferably 4.3 to 4.8, and a produced insoluble fraction is collected to obtain a soybean 7S protein with a high purification degree.

A method for preparing the soybean 7S protein is not limited to said method, and optionally, a conventional method for fractionating 7S may be used. For example, there is a method comprising adding NaCl to soybean milk from which 11S globulin has been removed to be a concentration of 0.25 M, adjusting the pH to 5.0, removing an insoluble fraction, adding a 3-fold volume of water to the insoluble fraction, adjusting the pH to 4.5, and collecting produced precipitates, as described in the method of Nagano et al. (see Non-Patent Document 6). Alternatively, there is a method comprising adjusting soybean milk from which 11S globulin has been removed to pH 2.8 to 3.5 by addition of sulfuric acid, removing produced precipitates, adding a 2-fold volume of water to a soluble fraction, adjusting the pH to 4.5, and recovering produced precipitates, as described in the method of Samoto et al. (see Non-Patent Document 5).

According to any of these methods, LP is prevented from getting mixed in with a 7S protein fraction, so that a soybean 7S protein having a high purity and good quality can be prepared.

Since the high purity soybean 7S protein thus obtained has a 7S purity of not lower than 80%, it is possible to make use of the property peculiar to 7S by using the soybean 7S protein. For example, the soybean 7S protein can be utilized in a nutrient functional agent such as a blood neutral fat reducing agent or a body fat reducing agent, or a highly viscous material.

In addition, the soybean 7S protein thus obtained has such an extremely low LCI content as not more than 30%, more preferably not more than 25%, further preferably not more than 20%, and is excellent in flavor.

(4) Soybean Curd Refuse

The soybean curd refuse of the present invention is obtained by extracting the processed soybean of the present invention as raw material with water, and recovering an insoluble fraction.

Since LP contained in the processed soybean of the present invention is selectively water-insolubilized, when the processed soybean is extracted with water as described above, 7S and 11S are mainly extracted into soybean milk, and LP is mainly extracted into soybean curd refuse.

Therefore, the soybean curd refuse of the present invention is characterized by rich LP. The LP content of the soybean curd refuse of the present invention is 35 to 60% by weight in a dry solid matter. In contrast, the LP content of conventional soybean curd refuse is about 10 to about 20% by weight in a dry solid matter. Among soybean acid-precipitable soybean proteins, LP particularly has an excellent blood cholesterol lowering activity. Thus, according to the present invention, it is possible to add highly a value to soybean curd refuse which is generally discarded as a by-product of soybean milk.

The soybean cued refuse of the present invention is obtained by collected the insoluble fraction separated during the preparation of soybean milk as describe above by centrifugation or the like. The soybean cued refuse can be optionally subjected to treatment such as sterilization, freezing, grinding, drying and the like to make various forms of products.

(5) Non-7S/11S-Acid-Precipitable Soybean Protein (LP-SPI)

It has been believed that LP contributes to deterioration of the flavor of a conventional soybean protein material. However, a non-7S/11S-acid-precipitable soybean protein obtained by highly fractionating LP has various applications in which the property peculiar to LP is utilized.

The LP-SPI of the present invention can be obtained by two fractionation methods of the case of using soybean curd refuse prepared from the above-described processed soybean as raw material and the case of using soybean milk as raw material.

The first method for preparing LP comprises fractionation of soybean curd refuse prepared from the above-described processed soybean. The LP fraction thus obtained has an oil content of not less than 7%, preferably not less than 8%, wherein the oil component is extracted with a mixture of chloroform and methanol at a volume ration of 2:1 as a solvent. A preparation example will be shown below.

[Preparation Example of LP-SPI]

Since LP contained in the processed soybean of the present invention is selectively insolubilized, LP can be obtained by extracting soybean milk from the processed soybean to obtain soybean curd refuse as a residue, and then fractionating the soybean curd refuse.

Fractionation can be attained by adding water to the soybean curd refuse, followed by hot extraction, and then collecting the extract. The addition amount of water is preferably 50 to 500 parts by weight per 100 parts by weight of the soybean curd refuse. The heating temperature is preferably 100 to 150° C. The heating time is preferably between a few seconds and a few minutes.

According to the above-described method, LP-SPI having LCI of not less than 50% by weight, preferably not less than 60% by weight can be provided as an extract. In addition, LP-SPI with a higher purity can be obtained by adding adjusting the extract to pH to 4 to 5, preferably pH 4.3 to 4.8 by addition of an acid and collecting produced precipitates. The precipitates are neutralized with sodium hydroxide to prepare a neutralized solution, which is sterilized, heated and dried. According to the above-described method, LP-SPI can be provided as a high purity product having LCI of not less than 60% by weight, preferably not less than 65% by weight.

The second method for preparing LP comprises fractionation of soybean milk prepared from the above-described processed soybean. The LP fraction thus obtained has an oil content of not less than 7%, preferably not less than 8%, wherein the oil component is extracted with a mixture of chloroform and methanol at a volume ration of 2:1 as a solvent. A preparation example will be shown below.

[Preparation Example of LP-SPI]

About 50 to 80% of the total content of LP in the processed soybean of the present invention is selectively insolubilized, and about 20 to 50% of the total content is extracted into soybean milk. Therefore, it is also possible to fractionate LP from soybean milk prepared from the processed soybean of the present invention.

Specifically, a high purity LP fraction can be obtained by collecting an insoluble fraction produced when soybean milk prepared from the processed soybean of the present invention is adjusted to pH 5.2 to 6.4, an insoluble fraction is separated to obtain a water-soluble fraction, and the water-soluble fraction is adjusted to pH 4 to 5.5, heated at 40 to 65° C. and then adjusted to pH 5.3 to 5.7, in the above-described process for preparing a soybean 7S protein from the processed soybean of the present invention.

In the case of using a 7S globulin-deficient soybean, a step for separating 7S and LP is not needed, and thus a fractionation operation is simpler. Specifically, a high purity LP fraction can be obtained simply by adjusting soybean milk prepared from the processed soybean to pH 5.2 to 6.4, separating an insoluble fraction (11S fraction) to obtain a water-soluble fraction, adjusting the water-soluble fraction to pH 4 to 5, and collecting an insoluble fraction.

The fraction obtained by the above-described method is neutralized with sodium hydroxide to prepare a neutralized solution if necessary, sterilized, heated and then dried.

According to the above-described method, LP-SPI can be provided as a high purity product having LCI of not less than 60% by weight.

The LP fractionated by the two methods as described above has strong affinity for lipids. Therefore, whether a soybean protein material corresponds to the LP-SPI of the present invention or not can be determined by whether the content of an oil component in the protein is not less than 7% by weight, preferably 8 to 15% by weight, more preferably 9 to 15% by weight wherein the oil component is extracted with a 2:1 mixture of chloroform:methanol as a solvent (hereinafter, referred to as the "chloroform-methanol oil content"). However, when LP-SPI contains not less than 2% of an oil component which is extracted with ether, the content of the ether-extracted oil component must be subtracted from a numerical value of the chloroform-methanol oil content. The extracted polar lipid comprises mainly lecithin and glycolipid.

Incidentally, a conventional isolated soybean protein which is not fractionated has a chloroform-methanol oil content of about 4 to about 5% by weight, and a high purity soybean 7S protein and a high purity soybean 11S protein have merely a chloroform-methanol oil content of not more than 3%.

[Blood Cholesterol Lowering Composition Comprising LP-SPI]

A blood cholesterol lowering composition can be obtained by incorporation of LP-SPI obtained according to the present invention into the composition. Any LP-SPI has a blood cholesterol lowering activity, regardless of which of the above-described methods is used for fractionation.

The present inventors confirmed the effect of LP-SPI on the blood cholesterol concentration of a rat when LP-SPI was given to the rat. As a result, LP-SPI exhibited a remarkably stronger blood cholesterol lowering action, as compared with an isolated soybean protein, a soybean 7S protein and a soybean 11S protein. In addition, it was also confirmed that 7S having a high purity, that is, 7S having a low LP content used in said test exhibited little blood cholesterol lowering action.

Further, it was confirmed that a product obtained by washing LP-SPI with ethanol once to remove a chloroform-methanol extract, and adding again the chloroform-methanol extract thereto exhibited less blood cholesterol lowering action than that of LP-SPI before washing with ethanol.

Thus, LP-SPI exhibits a strong cholesterol lowering action because of the coexistence of LP and a chloroform-methanol extract and the presence of them as a complex in LP-SPI.

The amount of LP-SPI to be contained in the blood cholesterol lowering composition of the present invention can be appropriately determined depending on the form and amount of the composition. Usually, a person skilled in the art may determine the content of LP-SPI in the composition by considering the amount ingested per day of the composition so that the amount of an active ingredient to be ingested per day can be taken. For example, in the case where the amount of LP-SPI to be ingested per day is 4.5 g and the amount of the composition to be ingested per day is 10 g, the content of an active ingredient in the composition may be 45% by weight. The amount of LP-SPI of the present invention to be ingested per day is not particularly limited, but it may be 4 to 10 g.

The blood cholesterol lowering composition of the present invention may contain, in combination with LP-SPI, an ingredient which is said to have a blood cholesterol lowering activity. For example, isoflavone, soybean milk, an isolated soybean protein, a concentrated soybean protein, lecithin, a lactic acid bacterium, polyphenol, polysaccharide or the like may be contained.

The blood cholesterol lowering composition of the present invention can take the form of an agent or a food.

In the case of an agent, the composition of the present invention can be formulated into various dosage forms of preparations. In the case of oral administration, the composition of the present invention can be administered in a form of a solid preparation such as a tablet, a hard capsule, a soft capsule, a granule and a pill, or a liquid preparation such as a solution, an emulsion and a suspension. In the case of parenteral administration, the composition of the present invention is administered in a form of an injection solution, a suppository or the like. For formulation of these preparations, additives which are acceptable for formulation, for example, excipients, stabilizers, preservatives, wetting agents, emulsifiers, lubricants, sweeteners, coloring agents, perfumes, tonicity regulating agents, buffers, antioxidants, pH adjusting agents and the like can be used in combination.

In the case of a food, the composition of the present invention can be incorporated into various foods such as soft drinks, milk products, soybean milk, fermented soybean milk, soybean protein drinks, bean curd (tofu), fermented soybeans (natto), thin deep-fried bean curd (aburaage), thick deep-fried bean curd (atsuage), deep-fried bean curds containing bits of various kinds of vegetables (ganmodoki), hamburgers, meatballs, deep-fried chickens, nuggets, various daily dishes, confectionery such as baked confectionery, nutrient bars, cereals, candies, gums, jellies and the like, tablets, breads, cooked rice and the like, which are general forms of foods. Further, in the case of a food, the composition of the present invention can be also incorporated into health foods such as food for specified health use in Japan, and a package or an advertising medium such as a pamphlet of the food can indicate directly or indirectly that said food contains LP-SPI as an active ingredient and thereby said food has a blood cholesterol lowering activity.

As explained above, a first advantage of the present invention is that selective water-insolubilization of LP facilitates efficient fractionation of 7S, 11S and LP with a high purity, which previously needed a complicated operation. Using the processed soybean of the present invention as raw material, it is possible to fractionate a mixture of 7S and 11S at a high purity by only precipitating the components at respective specific isoelectric points. In addition, it is possible to fractionate LP which has not been previously recognized much, at a high purity. The LP-SPI containing the LP at a high concentration has a stronger blood cholesterol lowering activity than that of an isolated soybean protein, and can be provided as a novel soybean protein material.

A second advantage of the present invention is that the flavors of existing soybean protein materials such as soybean milk and an isolated soybean protein can be improved. That is, LP is selectively insolubilized by the soybean processing-treatment of the present invention, so that the state where lipids associating with LP are hardly extracted can be led. Thus, the flavors of extracted soybean milk and various soybean protein materials prepared from the soybean milk are considerably improved.

At the same time, the selective water-insolubilization treatment of LP causes inactivation of endogenous enzymes of soybeans, such as lipoxygenase which is involved in lipid deterioration. In particular, contact with an aqueous polar organic solvent leads to inactivation of an enzyme system, so that generation of off-flavors during extraction can be suppressed. The off-flavors are smell components produced during processing, and are mainly aldehydes and ketones, so-called carbonyl compounds, which are generated by enzymatic or chemical oxidation reaction of unsaturated fatty acids of lipids. These lead to unpleasant flavors. The processed soybean of the present invention is also characterized by a very small amount of carbonyl compound production.

Further, in the processed soybean of the present invention, the number of bacteria is decreased because of the processing treatment. This results in suppression of bacterial proliferation during a processing treatment using water. Therefore, the processed soybean of the present invention is advantageous not only from a viewpoint of flavor, but also from a viewpoint of hygiene.

Since soybean milk obtained from the processed soybean of the present invention has a good flavor, it can be provided as a high quality soybean milk material. Further, an isolated soybean protein, a soybean 7S protein and a soybean 11S protein which are prepared by fractionation of the soybean milk have a remarkably good color and flavor and, for example, even if they are subjected to a severe heating treatment such as retort sterilization, their color is not blackened and their flavor is not deteriorated.

In addition, the processing treatment of the present invention using a polar alcohol that causes inactivation of an enzyme involved in oxidation degradation and decrease of bacteria can be applied to not only defatted soybeans, but also to whole fat soybeans. Therefore, the present invention is also very effective in improving the flavor of soybean milk prepared from whole fat soybeans.

EXAMPLES

Examples of the present invention will be described below, but the present invention is not limited to Examples, and various changes can be made in a range without departing from the gist of the present invention.

<Preparation of Processed Defatted Soybean>

Example 1

Ethanol Treatment 1

In a sealed container, 100 g of aqueous ethanol (10%, 50%, 60%, 70%, or 80%) was sprayed on 1 kg of a low-denatured defatted soybean (PDI: 83, water content: 7.0%) while mixing. The outside of the sealed container was heated so that the defatted soybean became a product temperature of 70° C., and then was maintained for 30 minutes. The defatted soybean was taken out of the container, and allowed to cool to obtain a processed defatted soybean. The processed defatted soybeans thus obtained had PDI of 71, 67, 64, 65 and 64, respectively.

Example 2

Ethanol Treatment 2

A processed defatted soybean was prepared in the same manner as in Example 1 except that the amount of aqueous ethanol (70%) sprayed was increased to 150 g. The processed defatted soybean had PDI of 72.

Example 3

Ethanol Treatment 3

A processed defatted soybean was prepared in the same manner as in Example 1 except that the amount of aqueous ethanol (70%) sprayed was increased to 200 g. The processed defatted soybean had PDI of 45.

Example 4

Wet Heating Treatment 1

The outside of a sealed container containing 1 kg of a defatted soybean (PDI: 83, water content: 7.0%) under an atmosphere of a relative humidity of not less than 90% was heated so that the defatted soybean became a product temperature of 75° C., and then was maintained for 30 minutes. The defatted soybean was taken out of the container to obtain a processed defatted soybean. The processed defatted soybean had PDI of 73.

Example 5

Wet Heating Treatment 2

A processed defatted soybean was prepared in the same manner as in Example 4 except that the outside of a container was heated so that a defatted soybean became a product temperature of 85° C. and then was maintained for 60 minutes. The processed defatted soybean had PDI of 66.

Example 6

Ethanol Treatment 4

A processed defatted soybean was prepared in the same manner as in Example 1 except that the amount of aqueous ethanol (70%) sprayed was decreased to 30 g. The processed defatted soybean had PDI of 79.

Comparative Example 1

Ethanol Treatment 5

A processed defatted soybean was prepared in the same manner as in Example 1 except that the amount of aqueous ethanol (80%) sprayed was increased to 1.5 kg and the heating maintenance time was extended to 60 minutes. The processed defatted soybean had PDI of 32.

Comparative Experiment Example 1

Preparation and Component Analysis of Defatted Soybean Milk

In this Example, whether the processed defatted soybeans obtained in Examples 1 to 6 and Comparative Example 1 had the characteristic that only LP was selectively insolubilized was examined. According to the above-described (Method 1), soybean curd refuse was separated from the defatted soybean to prepare soybean milk. According to the (Method 2), a whey fraction was separated from the soybean milk, and the residual fraction was further fractionated into a 7S and 11S fraction (MSP fraction) and a LP fraction.

Then, the nitrogen amounts of the whey fraction, the soybean curd refuse fraction, the LP fraction and the MSP fraction thus obtained were analyzed by a Kjeldahl method, and the rate of nitrogen transferred into each fraction (%) was calculated, assuming the total nitrogen amount contained in the defatted soybean to be 100%. Then, a selective water-insolubilization index which is a nitrogen ratio (LP/MSP) between the LP fraction and the MSP fraction was calculated.

Similarly, as a control, soybean milk was extracted from a low-denatured defatted soybean which had not been subjected to the processing treatment, and then analyzed. Results are shown in Table 2.

untreated control. Thus, it was confirmed that 7S and 11S were extracted into a soybean milk side at a high yield.

As seen from results of Examples 1 to 3, Example 6, and Comparative Example 1, when the ethanol concentration was higher and the ethanol addition amount was larger, a lower PDI value was showed and the denaturation degree of the defatted soybean was increased. On the other hand, when the ethanol addition amount was increased to some extent, a decreasing trend of the nitrogen transfer rate into a LP fraction became smaller and, conversely, the nitrogen transfer rate into MSP tended to decrease. As a result, LP/MSP tended to increase. In Comparative Example 1, LP/MSP was the same as that of the control.

In Examples 4 and 5 of the defatted soybean processing method using wet heating, PDI values nearly equal to those in the case of using ethanol addition were obtained, and LP was selectively water-insolubilized. In Example 5 in which strongly heated, the nitrogen transfer rate into a MSP fraction was decreasing, and the LP/MSP ratio was slightly higher than that in the case of using ethanol addition. In comparison between the wet heating case and the ethanol addition case, LP/MSP was smaller in the ethanol addition case, and there was a tendency that LP was more selectively water-insolubilized.

As seen from the above results, a preferable condition of a defatted soybean processing treatment for selective water-insolubilization of LP was a condition that could produce a processed soybean having PDI of not less than 40 and less

TABLE 2

Analysis results of soybean milk extracted from various processed defatted soybeans

| | Processing method | Ethanol addition amount | Wet heating time | PDI | Nitrogen transfer rate | | | | LP/MSP |
| --- | --- | --- | --- | --- | --- | --- | --- | --- | --- |
| | | | | | Whey | MSP (7S · 11S) | LP | Soybean curd refuse | |
| Control | Untreated | 0% | — | 83 | 10 | 48 | 23 | 19 | 48% |
| Example 1 | 10% ethanol | 10% | — | 71 | 10 | 48 | 14 | 28 | 29% |
| | 50% ethanol | 10% | — | 67 | 10 | 48 | 13 | 29 | 27% |
| | 60% ethanol | 10% | — | 64 | 10 | 48 | 12 | 30 | 25% |
| | 70% ethanol | 10% | — | 65 | 9 | 48 | 12 | 31 | 25% |
| | 80% ethanol | 10% | — | 64 | 9 | 48 | 12 | 31 | 25% |
| Example 2 | 70% ethanol | 15% | — | 72 | 9 | 46 | 9 | 36 | 20% |
| Example 3 | 70% ethanol | 20% | — | 45 | 9 | 36 | 10 | 45 | 28% |
| Example 4 | wet heating 75° C. | — | 30 min | 73 | 10 | 48 | 18 | 24 | 38% |
| Example 5 | wet heating 85° C. | — | 60 min | 66 | 10 | 39 | 12 | 39 | 31% |
| Example 6 | 70% ethanol | 3% | — | 79 | 10 | 48 | 20 | 22 | 42% |
| Comparative Example 1 | 80% ethanol | 150% | — | 32 | 9 | 25 | 12 | 54 | 48% |

As seen from the experimental results, the soybean milk extracted from the processed defatted soybeans under the treatment condition shown in Examples 1 to 6 exhibited remarkably low selective water-insolubilization indexes (LP/MSP) as compared with Comparative Example 1 and the control. Thus, it was confirmed that LP contained in the processed defatted soybean was selectively insolubilized, and about 50 to about 80% of the LP remained in a soybean curd refuse fraction when it was tried to be extracted with water.

Although in a few Examples, for example, in Example 3, the rate of nitrogen transferred into MSP was decreased and the yield was decreased, in almost all of Examples, the nitrogen transfer rate into MSP was not less than 45%, which was close to 48%, the nitrogen transfer rate into MSP of the than 80 and LP/MSP of not more than 45%. As specific examples of a processing treatment method satisfying such a condition, a method comprising controlling by wet heating and a method comprising adding 5 to 100% by weight of aqueous ethanol having a concentration of 5 to 100% to a soybean were suitable. Particularly, according to the method comprising addition of aqueous ethanol, LP/MSP could be decreased to 35% or less.

Comparative Experiment Example 2

Confirmation of Flavor of Soybean Milk and Isolated Soybean Protein Solution

The soybean milk prepared from each processed defatted soybean in Comparative Experiment Example 1 was boiled for 10 minutes, and cooled to room temperature to obtain soybean milk for a flavor test.

In addition, the soybean milk was adjusted to pH 4.5 with hydrochloric acid, and precipitates were collected by centrifugation to remove a whey fraction. The collected precipitates were neutralized with sodium hydroxide, and water was added to a concentration of 3%. The neutralized solution was boiled for 10 minutes, and cooled to room temperature to prepare an isolated soybean protein solution for a flavor test. The isolated soybean protein solution was subjected to analysis by SDS polyacrylamide gel electrophoresis under the condition shown in Table 1, and then, a LCI value (see Mathematical formula 1) which is an estimated LP content was calculated, according to the above-described method for estimating an LP content.

The soybean milk and the isolated soybean protein solution thus obtained were tested for their flavors by 10 panelists. On a score of 1 to 10, a higher score indicates less unpleasant flavor. As a standard, the score of a preparation example from an untreated soybean was determined to be 5. An average score obtained by dividing a sum score by the number of panelists is shown.

TABLE 3

Test for flavor of defatted soybean milk and isolated soybean protein solution prepared from each processed defatted soybean

| | Processing method | Defatted soybean milk | Isolated soybean protein | LCI value | Remark |
|---|---|---|---|---|---|
| Control | Untreated | 5 | 5 | 40 | Raw smell Miscellaneous taste |
| Example 1 | 10% ethanol | 7.1 | 7.3 | 30 | |
| | 50% ethanol | 7.6 | 7.5 | 29 | |
| | 60% ethanol | 7.8 | 7.1 | 27 | |
| | 70% ethanol | 7.3 | 8.2 | 25 | |
| | 80% ethanol | 7.7 | 7.6 | 25 | |
| Example 2 | 70% ethanol | 8.9 | 9.4 | 23 | Refreshing |
| Example 3 | 70% ethanol | 8.5 | 9.3 | 26 | |
| Example 4 | Wet heat 75° C. | 6.2 | 6.4 | 37 | |
| Example 5 | Wet heat 85° C. | 6.0 | 6.8 | 36 | Roasted-smell |
| Example 6 | 70% ethanol | 5.9 | 6.0 | 34 | |
| Comparative Example 1 | 80% ethanol | 8.2 | 9.3 | 39 | Low recovery |

The defatted soybean milk and isolated soybean protein solutions extracted from the processed defatted soybeans of Examples 1 to 3 and 6 (ethanol addition treatment) were assessed to have a refreshing flavor and little unpleasant taste. Also in Examples 4 and 5, the flavor was improved, but the improving effect was greater in the ethanol treatment. In Example 5 (wet heating treatment), scores were increased due to little miscellaneous taste, but a roasted smell was felt. In Comparative Example 1, the flavor was assessed as good, but the extraction amount of a MSP fraction was too small, which was a problem from a viewpoint of a production process.

Comparative Experiment Example 3

Preparation of Soybean 7S Protein and Soybean 11S Protein from Extracted Soybean Milk The soybean milk prepared from respective processed defatted soybeans in Comparative Experiment Example 1 was adjusted to pH 5.8 with hydrochloric acid, and produced precipitates were collected by centrifugation at 1000 G for 10 minutes. The insoluble fraction was used as a soybean 11S protein.

In addition, a water-soluble fraction after the centrifugation was further adjusted to pH 4.5 with hydrochloric acid, and a produced insoluble fraction was collected by centrifugation at 1000 G for 10 minutes. The insoluble fraction was used as a soybean 7S protein.

A solid matter (3.7 μg) of each protein as a sample was subjected to SDS-polyacrylamide gel electrophoresis with SDS-PAGE, and a purity test was performed. The purity test was performed by staining a gel with Coomassie Brilliant Blue, subjecting the gel to a densitometer, and calculating a ratio of the denseness of each band corresponding to 7S or 11S to the denseness of bands of all proteins. In addition, the LCI value of the sample was calculated. Results are shown in Table 4.

TABLE 4

Purity and recovery of soybean 11S protein and soybean 7S protein prepared from processed defatted soybean

| | Processing method | LP/MSP | Purity 11 S | Purity 7 S | Solid matter recovery* 11 S | Solid matter recovery* 7 S |
|---|---|---|---|---|---|---|
| Untreated | Untreated | 48% | 73% (31) | 37% (58) | 11% | 21% |
| Example 1 | 10% ethanol | 29% | 90% (19) | 50% (53) | 13% | 16% |
| | 50% ethanol | 27% | 92% (16) | 56% (50) | 13% | 14% |
| | 60% ethanol | 25% | 91% (19) | 53% (52) | 13% | 15% |
| | 70% ethanol | 25% | 92% (17) | 53% (52) | 13% | 15% |
| | 80% ethanol | 25% | 93% (15) | 53% (51) | 13% | 15% |
| Example 2 | 70% ethanol | 20% | 96% (12) | 62% (45) | 13% | 13% |
| Example 3 | 70% ethanol | 28% | 97% (11) | 64% (43) | 12% | 11% |
| Example 4 | Wet heat | 38% | 85% (28) | 46% (55) | 12% | 18% |
| Example 5 | Wet heat | 31% | 75% (34) | 38% (57) | 10% | 16% |
| Example 6 | 70% ethanol | 42% | 85% (28) | 45% (56) | 12% | 20% |
| Comparative Example 1 | 80% ethanol | 48% | 90% (20) | 41% (58) | 6% | 9% |

*Solid matter recovery assuming that solid content of defatted soybean is 100%

Numerical value in ( ): LCI value

In all Examples, the purity of the soybean 11S protein was as high as not less than 75%, in particular, in Examples 1 to 3 the purity of the soybean 11S protein was as high as not less than 90%, and the recovery of the soybean 11S protein was equal or more to that of the untreated preparation. The purity of the soybean 7S protein was not less than 38% in all Examples, in particular, it was not less than 50% in Examples 1 to 3, and it exceeded 60% in some Examples. These proteins were assessed to have a refreshing flavor and little unpleasant taste.

In Comparative Example 1, the purity of the soybean 11S protein was nearly equal to that in Examples, but the recovery of the soybean 11S protein was considerably decreased to 6%. This is probably because the amounts of 7S and 11S transferred into soybean curd refuse were large, and selective water-insolubilization of LP was insufficient.

Example 7

Preparation of High Purity Soybean 7S Protein

In order to increase purity, a soybean 7S protein can be subjected to the following method.

After a soybean 11S protein was obtained from the processed defatted soybean prepared in Example 2 according to Comparative Experiment Example 3, the remaining water-soluble fraction was adjusted to pH 5.0 with hydrochloric acid, heated at 60° C. for 15 minutes, adjusted to pH 5.5 with sodium hydroxide, stirred with a propeller (300 to 350 rpm) for 30 minutes, and then centrifuged at 1000 G for 10 minutes to remove an insoluble fraction A (FIG. 4: 7S impurities). The supernatant was adjusted to pH 4.5 with hydrochloric acid, and a produced insoluble fraction B was collected by centrifugation at 1000 G for 10 minutes. The insoluble fraction B was used as a soybean 7S protein, and subjected to a purity test with SDS-PAGE according to Comparative Experiment Example 3. As a result, the purity of the soybean 7S protein was 91% (FIG. 4: 7S globulin). In addition, the LCI value was 12.

The protein was assessed to have a refreshing flavor and little unpleasant taste.

Example 8

Preparation 1 of LP-SPI

After soybean milk was extracted from the processed defatted soybean prepared in Example 2 according to Comparative Experiment Example 2, an equal weight of water was added to soybean curd refuse, heated at 110° C. for 30 seconds, and then centrifuged (1000 g, 10 min) to collect a water-soluble fraction. The water-soluble-fraction was adjusted to pH 4.5 by addition of hydrochloric acid, and a produced insoluble fraction was collected by centrifugation (1000 g, 10 min). The insoluble fraction was used as LP-SPI (FIG. 4: lane LP). Regarding an oil component contained in a solid matter of the protein, the amount of an oil component extracted with ether was 1%, and the amount of an oil component extracted with a 2:1 solvent mixture of chloroform:methanol was 11%. It was shown that the protein contained a large amount of LP having affinity for polar lipids.

Since the resulting LP-SPI contained a large amount of LP which had been believed to be a causative component for off-flavors of an isolated soybean protein, it was expected that the LP-SPI had an unpleasant flavor. However, when the LP-SPI actually tested for flavor, it unexpectedly had a good flavor and no unpleasant flavor. At this time, the LCI value was 72%.

Example 9

Preparation 2 of LP-SPI

An insoluble fraction A obtained by the same method as that of Example 7 was collected, and this fraction was used as LP-SPI. Regarding an oil component contained in a solid matter of the protein, the amount of an oil component extracted with ether was 1%, and the amount of an oil component extracted with a 2:1 solvent mixture of chloroform:methanol was 9%. It was shown that the protein contained a large amount of LP having affinity for polar lipids.

The resulting LP-SPI, similarly to the LP-SPI of Example 7, unexpectedly exhibited a good flavor and no unpleasant flavor. At this time, the LCI value was 71%.

Nutrient Test 1: Confirmation of Blood Cholesterol Lowering Activity of LP-SPI The blood cholesterol lowering activity of various soybean protein materials obtained in Comparative Experiment Example 3, Example 6 and Example 7 was confirmed.

A diet containing 20% by weight of casein "Vitamin-Free Casein" (manufactured by Oriental Yeast, hereinafter described as "casein") on the basis of AIN-93G composition (REEVES P. G. et al., J. NUTR, 123, 1939-1951, 1993) was used as a control. A test diet (Table 5) was prepared by substituting (1) an isolated soybean protein "Fujipro F" (manufactured by FUJI OIL COMPANY, Limited), (2) a soybean 11S protein produced as described in Comparative Experiment Example 3, (3) a soybean 7S protein produced as described in Example 7, (4) LP-SPI produced as described in Example 8, or (5) LP-SPI produced as described in Example 9 for 10% by weight of the protein source of the control diet. These diets were given to model animals in an amount of 2 g per day of protein, by the following method.

As model animals, 36 WISTAR male rats aged 6 weeks (sold by Japan SLC) were used. After pre-rearing for a week, the animals were grouped into 6 animals per group so that the average body weight between groups became approximately equal, and were reared with test diets for two weeks.

TABLE 5

| Blending | Test group | Casein group (control group) |
|---|---|---|
| Soybean protein material | 10.0 | — |
| Casein | 10.0 | 20.0 |
| Sucrose | 10.0 | 10.0 |
| B corn starch | 39.4 | 39.4 |
| A corn starch | 13.2 | 13.2 |
| Soybean oil | 7.0 | 7.0 |
| Vitamin mixture* | 1.0 | 1.0 |
| Mineral mixture** | 3.5 | 3.5 |
| Cellulose | 5.0 | 5.0 |
| Bitartaric acid choline | 0.25 | 0.25 |
| Cholesterol | 0.5 | 0.5 |
| Sodium cholate | 0.125 | 0.125 |
| Total | 100 | 100 |

*AIN-93 composition,
**AIN-93G composition

After termination of the test period, the animals were fasted for 6 hours from 8:00 morning, and then, their abdomens were opened under nembutanol anesthesia to withdraw blood from an abdominal aorta. After heparin treatment, the blood was centrifuged at 3000 RPM for 15 minutes. The resulting plasma was subjected as a sample to measurement of blood total cholesterol (TC) and a fecal steroid excretion amount.

TC was measured using a Fuji Drichem 5500 (Fuji Photo Film Co., Ltd.). A fecal steroid excretion amount was calculated by collecting feces for three days before slaughter, lyophilizing and grinding the feces, analyzing excreted neutral and acidic steroids by gas chromatography according to the method of Miettinen et al. (Miettinen, T. A.; Ahrens, E. H. Jr.; Grundy, S. M. Quantitative isolation and gas-liquid chromatographic analysis of total dietary and fecal neutral steroids. J. Lipids Res., 6, 411-424, 1965) and the method of Grundy et al. (Grundy, S. M.; Ahrens, E. H. Jr.; Miettinen, T. A. Quantitative isolation and gas-liquid chromatographic analysis of total fecal bile acids. J. Lipid Res., 6, 397-410, 1965.), and then summing the obtained values.

Results concerning a change in the cholesterol level and the fecal total steroid excretion amount in rats which were reared with test diets for two weeks are shown in Table 6.

TABLE 6

Result: Change in cholesterol level in rats which were reared with test diets for two weeks

| | Chloform-Methanol extraction amount | LCI value | TC (mg/dl) | total fecal steroid excretion amount (mg/day) |
|---|---|---|---|---|
| LP-SPI group (Example 8) | 11.2% | 72% | 137 ± 9a | 83.9 ± 1.8ab |
| LP-SPI group (Example 9) | 9.3% | 71% | 139 ± 8a | 88.6 ± 3.8a |
| SPI group (Fujipro F) | 4.5% | 39% | 176 ± 4bc | 73.7 ± 2.9ab |
| 11S group | 2.1% | 14% | 166 ± 9ab | 74.8 ± 4.3ab |
| 7S group | 0.5% | 12% | 202 ± 5c | 79.0 ± 4.4ab |
| Control group (casein) | — | — | 199 ± 12bc | 68.5 ± 4.8c |

(Remark) Significant difference test: There is a significant difference between different symbols of respective groups (P < 0.05).

As seen from the above results, ingestion of LP-SPI significantly lowered the blood cholesterol level as compared with an isolated soybean protein and a soybean 7S protein. Further, as compared with a soybean 11S protein, LP-SPI had a tendency to lower the blood cholesterol level. Thus, it was found that LP-SPI fractionated by the method of the present invention was a material having a stronger blood cholesterol lowering activity than a conventional soybean protein material.

Nutrient Test 2

Next, LP-SPI was washed with ethanol to remove a chloroform-methanol extract, and influence of said removal on the blood cholesterol lowering activity of LP-SPI was examined.

LP-SPI prepared as in Example 8 was washed with a 10-fold volume of 70% ethanol once, a 3-fold volume of 70% ethanol once, and then a 2-fold volume of 99.5% ethanol. After dried at room temperature overnight, the LP-SPI was dried at 60° C. for an hour to obtain ethanol-washed LP-SPI (LP-EW). LP-EW contained 1.4% of a chloroform-methanol extract.

Then, ethanol was evaporated from the ethanol washing solution with an evaporator (at 50 to 55° C.), and the residue was lyophilized to obtain a lipid. The lipid was dissolved in the soybean oil shown in Table 5, which was used in combination with LP-EW to prepare a test diet as a sample (LP-EW+Lipid) wherein the lipid and LP-EW were mixed again.

In the same manner as in Nutrient Test 1, a diet containing 20% by weight of casein was used as a control, and a test diet (Table 5) was prepared by substituting LP-SPI, LP-EW, or LP-EW+Lipid for 10% by weight of the protein source. These diets were given to model animals in an amount of 2 g per day of protein by the following method. Respective protein ingestion groups were a casein group (control group), an LP-SPI group, an LP-EW group, and an LP-EW+Lipid group. Model animals were 24 WISTAR male rats aged 6 weeks (sold by Japan SLC). After pre-rearing for a week, the animals were grouped into 6 animals per group so that the average body weight between groups became approximately equal, and were reared with test diets for two weeks. After termination of the test period, a change in the blood cholesterol level of rats which were reared with test diets for 2 weeks were examined in the same manner as in Nutrient Test 1. Results are shown in Table 7.

TABLE 7

Change in cholesterol level of rats reared with test diets for 2 weeks

| | TC (mg/dl) |
|---|---|
| LP-SPI group | 166 ± 6a |
| LP-EW group | 192 ± 6b |
| LP-EW + Lipid group | 250 ± 18c |
| Control group (casein) | 204 ± 8b |

(Remark) Significant difference test: There is a significant difference between different symbols of respective groups (P < 0.05).

As seen from the results of Table 7, once a chloroform-methanol extract was removed from LP-SPI with ethanol, the LP-SPI lost the strong blood cholesterol lowering activity even if the chloroform-methanol extract was mixed again with the LP-SPI. Therefore, it is thought that the LP-SPI of the present invention exhibits a stronger blood cholesterol lowering activity when a chloroform-methanol extract having high affinity for LP such as lecithin coexists and forms a complex with LP than when LP exists alone.

INDUSTRIAL APPLICABILITY

Using the processed soybean of the present invention as raw material, it is possible to simply fractionate a soybean protein into 7S globulin, 11S globulin and a lipophilic protein with a high purity, and thereby a complicated production process of a conventional fractionation method can be considerably improved.

In addition, the present invention can provide a soybean 7S protein, a soybean 11S protein and a non-7S/11S-acid-precipitable soybean protein with a high purity, and thereby it becomes possible to produce foods in which the physical properties and nutrient physiological functions of these proteins are more utilized. Particularly, the non-7S/11S-acid-precipitable soybean protein is a novel soybean protein material which has not been commercialized previously. Since the non-7S/11S-acid-precipitable soybean protein has a higher cholesterol lowering activity than conventional isolated soybean proteins, it is expected to be used for a nutrition improvement purpose, for example, used in food for specified health use.

Further, since the soybean milk, the isolated soybean protein, the soybean 7S protein, the soybean 11S protein, the soybean curd refuse and the non-7S/11S-acid-precipitable soybean protein obtained by the present invention have a very better flavor than conventional soybean protein materials, they have a great utility value in improving the quality of conventional foods produced using conventional soybean protein materials.

Figure 1:
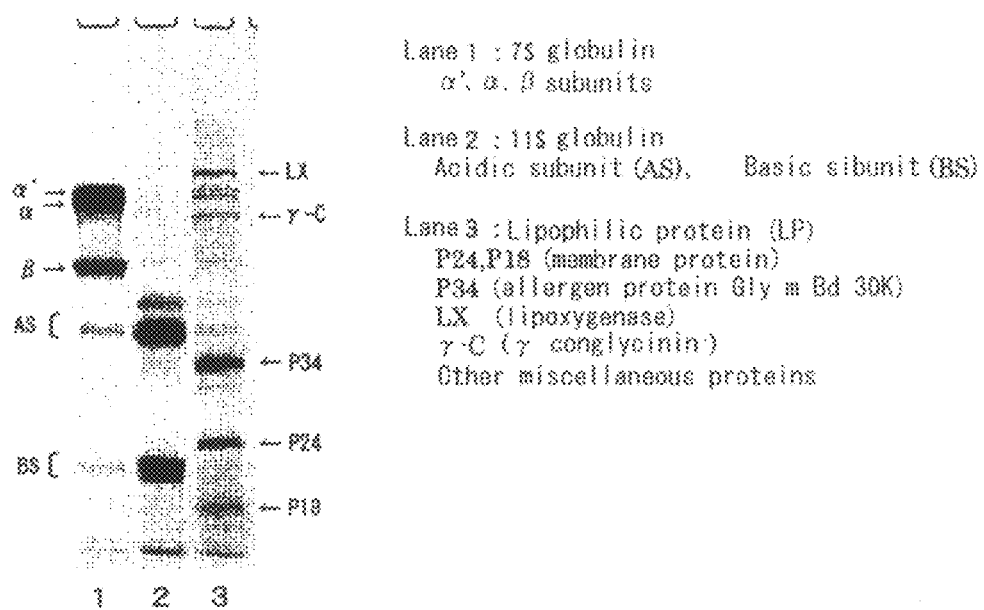
FIG. 1 is a graph showing dissolution behavior of 7S globulin and 11S globulin at each pH.
Figure 2:
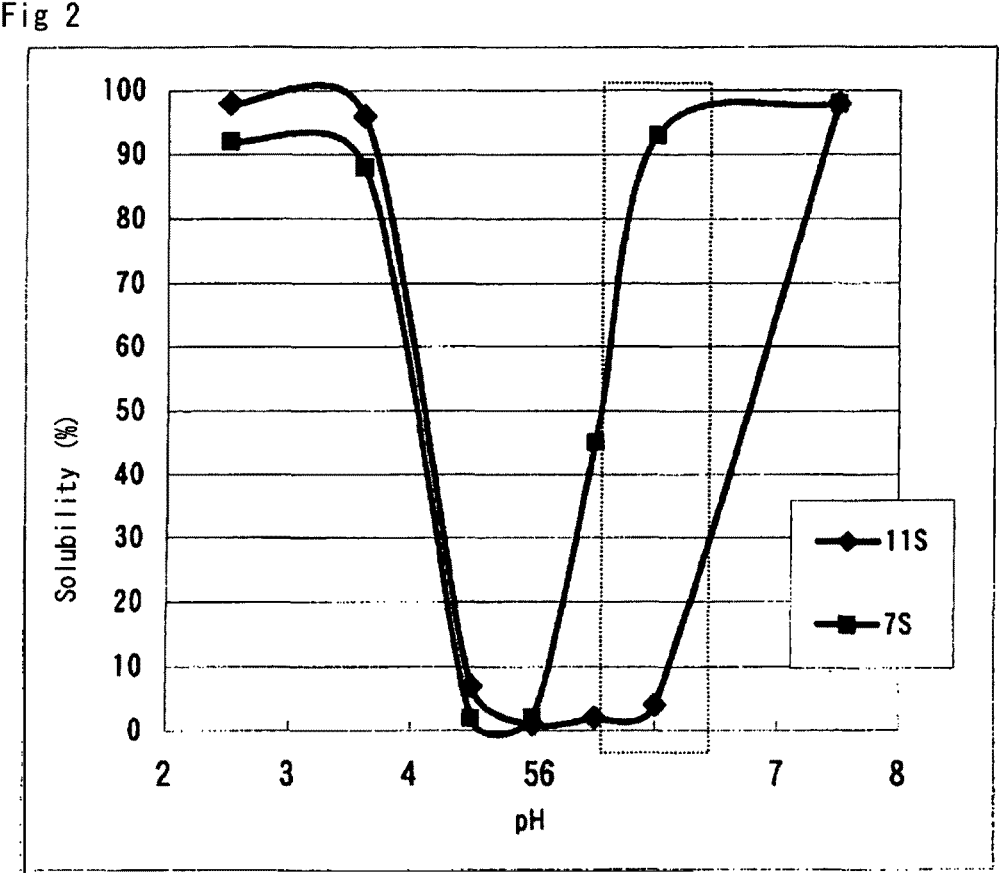
FIG. 2 is a photograph which is a substitute for a drawing, showing electrophoretic patterns of a 7S globulin fraction, an 11S globulin fraction and a lipophilic protein fraction by SDS-polyacrylamide gel electrophoresis.
Figure 3:
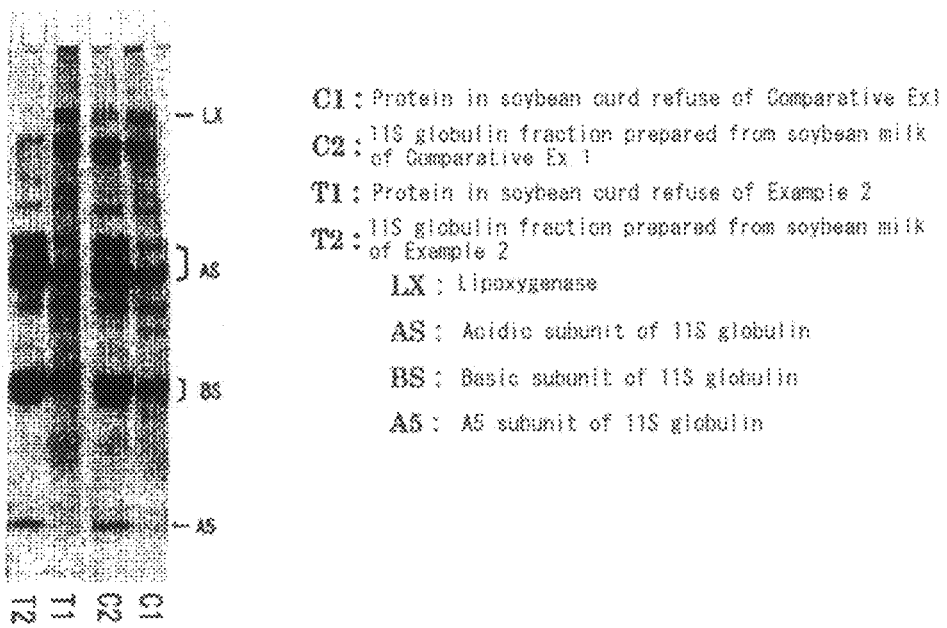
FIG. 3 is a photograph which is a substitute for a drawing, showing electrophoretic patterns of soybean 11S globulin proteins and soybean curd refuse prepared from the processed defatted soybeans of Example 2 and Comparative Example 1 by SDS-polyacrylamide gel electrophoresis.
Figure 4:
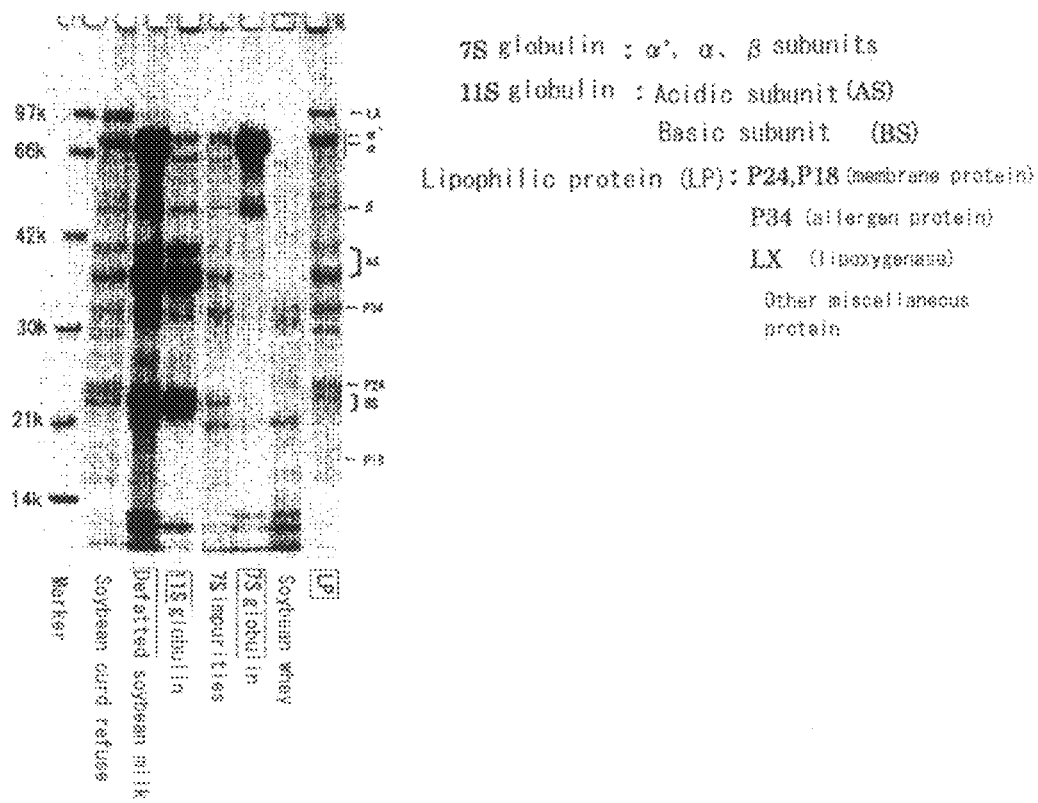
FIG. 4 is a photograph which is a substitute for ae drawing, showing electrophoretic patterns of respective fractions (soybean curd refuse, defatted soybean milk, 11S globulin, 7S impurities, 7S globulin, whey, lipophilic protein) prepared from the processed defatted soybean of Example 2 by SDS-polyacrylamide gel electrophoresis.

The invention claimed is:

1. A process for producing a fractionated soybean protein, which comprises preparing a processed soybean by subjecting a soybean comprising a protein component and a soybean curd refuse component to an impregnation with an equal or lesser weight of a polar alcohol solution and then to a warming treatment at a product temperature of 40 to 90° C., or by subjecting a soybean comprising a protein component and a soybean curd refuse component to a wet heating treatment, and preparing soybean milk or soybean curd refuse as raw material from the processed soybean, and then collecting, from the soybean milk or soybean curd refuse, a fraction in which at least an acid-precipitable soybean protein selected from the group consisting of 7S globulin, 11S globulin and a lipophilic protein is concentrated, wherein PDI of the processed soybean is not less than 40 and less than 80, and a lipophilic protein is selectively water-insolubilized among proteins contained in the processed soybean.

2. The process for producing a fractionated soybean protein according to claim 1, wherein the acid-precipitable soybean protein is a soybean 7S globulin protein which is obtained by fractionation of the soybean milk.

3. The process for producing a fractionated soybean protein according to claim 2, which further comprises adjusting the soybean milk to pH 5.2 to 6.4, separating an insoluble fraction to obtain a water-soluble fraction, adjusting the water-soluble fraction to pH 4 to 5.5, and then collecting an insoluble fraction produced.

4. The process for producing a fractionated soybean protein according to claim 3, which further comprises adjusting the water-soluble fraction to pH 4 to 5.5, heating the fraction at 40 to 65° C., adjusting the fraction to pH 5.3 to 5.7, separating an insoluble fraction produced to obtain a water-soluble fraction, adjusting the water-soluble fraction to pH 4 to 5, and then collecting an insoluble fraction produced.

5. The process for producing a fractionated soybean protein according to claim 2, which further comprises adjusting the soybean milk to pH 4 to 5.5, heating the soybean milk at 40 to 65° C., adjusting the soybean milk to pH 5.3 to 5.7, separating an insoluble fraction produced to obtain a water-soluble fraction, adjusting the water-soluble fraction to pH 4 to 5, and then collecting an insoluble fraction produced.

6. The process for producing a fractionated soybean protein according to claim 1, which further comprises adjusting the soybean milk to pH 4.2 to 5.2, and then collecting an insoluble fraction produced, wherein the fractionated soybean protein has a LCI value of not more than 38%.

7. The process for producing a fractionated soybean protein according to claim 1, wherein a selective water-insolublization index (LP/MSP) of the processed soybean is not more than 35%.

8. A method for fractionating a soybean protein, which comprises the following steps:
(1) preparing a processed soybean by subjecting a soybean comprising a protein component and a soybean curd refuse component to an impregnation with an equal or lesser weight of a polar alcohol solution and then to a warming treatment at a product temperature of 40 to 90° C., or by subjecting a soybean comprising a protein component and a soybean curd refuse component to a wet heating treatment,
(2) adding water to the processed soybean, and separating the mixture into soybean milk and soybean curd refuse;
(3) adjusting the soybean milk obtained in the step (2) to pH 5.2 to 6.4, and separating a water-soluble fraction to obtain a soybean 11S globulin protein as an insoluble fraction;
(4) adjusting the water-soluble fraction obtained in the step (3) to pH 4 to 5.5, heating the fraction at 40 to 65° C., and then adjusting the fraction to pH 5.3 to 5.7, and separating a water-soluble fraction produced to obtain a non-7S/11S-acid-precipitable soybean protein as an insoluble fraction; and
(5) adjusting the water-soluble fraction separated after adjustment to pH 5.3 to 5.7 in the step (4) to pH 4 to 5 to obtain a soybean 7S globulin protein as an insoluble fraction, wherein PDI of the processed soybean is not less than 40 and less than 80, and a lipophilic protein is selectively water-insolubilized among proteins contained in the processed soybean.

* * * * *